(12) United States Patent
Ueda et al.

(10) Patent No.: US 8,354,255 B2
(45) Date of Patent: Jan. 15, 2013

(54) L-AMINO ACID-PRODUCING BACTERIUM AND A METHOD FOR PRODUCING L-AMINO ACIDS

(75) Inventors: Takuji Ueda, Kawasaki (JP); Yuji Joe, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 875 days.

(21) Appl. No.: 12/056,390

(22) Filed: Mar. 27, 2008

(65) Prior Publication Data

US 2009/0275090 A1   Nov. 5, 2009

Related U.S. Application Data

(63) Continuation of application No. PCT/JP2006/319636, filed on Sep. 25, 2006.

(60) Provisional application No. 60/723,938, filed on Oct. 6, 2005.

(30) Foreign Application Priority Data

Sep. 27, 2005 (JP) .................................. 2005-279025
Dec. 14, 2005 (JP) .................................. 2005-360671

(51) Int. Cl.
C12P 13/14 (2006.01)
C12P 13/04 (2006.01)
C12P 13/08 (2006.01)

(52) U.S. Cl. .......................... 435/110; 435/106; 435/115
(58) Field of Classification Search ........................ None
See application file for complete search history.

(56) References Cited

U.S. PATENT DOCUMENTS

| 7,306,933 | B2 | 12/2007 | Van Dien et al. |
| 7,320,882 | B2 * | 1/2008 | Rieping ........................ 435/106 |
| 2006/0019355 | A1 | 1/2006 | Ueda et al. |
| 2006/0088919 | A1 | 4/2006 | Rybak et al. |
| 2006/0160191 | A1 | 7/2006 | Kataoka et al. |

OTHER PUBLICATIONS

Chica et al. (Curr Opin Biotechnol. Aug. 2005; 16(4):378-84.*
Bramley et al. (J. Gen. Microbiol 1987, 133, pp. 563-573).*
U.S. Appl. No. 11/759,419, filed Jun. 7, 2007, Ueda et al.
U.S. Appl. No. 11/877,726, filed Oct. 24, 2007, Van Dien et al.
U.S. Appl. No. 12/056,414, filed Mar. 27, 2008, Ueda et al.

* cited by examiner

*Primary Examiner* — Tekchand Saidha
*Assistant Examiner* — Md. Younus Meah
(74) *Attorney, Agent, or Firm* — Shelly Guest Cermak; Cermak Nakajima LLP

(57) ABSTRACT

A method for producing an L-amino acid is provided which includes culturing in a medium a microorganism of the Enterobacteriaceae family which has an ability to produce an L-amino acid and which has been modified so as to enhance the β-glucoside PTS activity, and collecting the L-amino acid from the medium or cells.

4 Claims, 3 Drawing Sheets

SEQUENCE LISTING

```
<160> NUMBER OF SEQ ID NOS: 49

<210> SEQ ID NO 1
<211> LENGTH: 31
<212> TYPE: DNA
<213> ORGANISM: Artificial Sequence
<220> FEATURE:
<223> OTHER INFORMATION: bglF primer 1
```

-continued

<400> SEQUENCE: 1
acacaagctt aggaggacaa gttatgacgg a                                31

<210> SEQ ID NO 2
<211> LENGTH: 33
<212> TYPE: DNA
<213> ORGANISM: Artificial Sequence
<220> FEATURE:
<223> OTHER INFORMATION: bglF primer2

<400> SEQUENCE: 2
gtgttctaga aaatctgagg tcgagatccc ttt                              33

<210> SEQ ID NO 3
<211> LENGTH: 31
<212> TYPE: DNA
<213> ORGANISM: Artificial Sequence
<220> FEATURE:
<223> OTHER INFORMATION: ptsG primer1

<400> SEQUENCE: 3
cacaaaagct tcatactcag gagcactctc a                                31

<210> SEQ ID NO 4
<211> LENGTH: 31
<212> TYPE: DNA
<213> ORGANISM: Artificial Sequence
<220> FEATURE:
<223> OTHER INFORMATION: ptsG primer2

<400> SEQUENCE: 4
gtgtgtctag aaactggcaa aatcgcgtgt a                                31

<210> SEQ ID NO 5
<211> LENGTH: 1878
<212> TYPE: DNA
<213> ORGANISM: Escherichia coli
<220> FEATURE:
<221> NAME/KEY: CDS
<222> LOCATION: (1)..(1878)

<400> SEQUENCE: 5

```
atg acg gag tta gcc aga aaa ata gtc gca gga gtc ggg ggc gca gat      48
Met Thr Glu Leu Ala Arg Lys Ile Val Ala Gly Val Gly Gly Ala Asp
1               5                   10                  15 aac att gtg agt ctg atg cat tgc gca acg cga tta cgt ttt aaa tta      96
Asn Ile Val Ser Leu Met His Cys Ala Thr Arg Leu Arg Phe Lys Leu
            20                  25                  30 aag gat gaa agc aaa gcg caa gca gag gta ctg aaa aag acc ccc ggt     144
Lys Asp Glu Ser Lys Ala Gln Ala Glu Val Leu Lys Lys Thr Pro Gly
        35                  40                  45 att att atg gtg gtg gaa agc ggt ggc cag ttt cag gtg gtc ata ggt     192
Ile Ile Met Val Val Glu Ser Gly Gly Gln Phe Gln Val Val Ile Gly
    50                  55                  60 aac cat gtg gcc gat gtc ttc ctg gcg gtt aac agt gtg gca ggc ctt     240
Asn His Val Ala Asp Val Phe Leu Ala Val Asn Ser Val Ala Gly Leu
65                  70                  75                  80 gac gaa aaa gcg caa cag gca ccg gaa aat gat gat aaa ggt aat ctg     288
Asp Glu Lys Ala Gln Gln Ala Pro Glu Asn Asp Asp Lys Gly Asn Leu
                85                  90                  95 cta aac cgc ttt gtt tat gtt att tca ggt att ttt acg cct ctg atc     336
Leu Asn Arg Phe Val Tyr Val Ile Ser Gly Ile Phe Thr Pro Leu Ile
            100                 105                 110
```

| | | | | | | | | | | | | | | | | |
|---|---|---|---|---|---|---|---|---|---|---|---|---|---|---|---|---|
| ggt | ttg | atg | gcg | gca | acc | ggg | atc | ttg | aaa | ggt | atg | ctg | gct | ctg | gcg | 384 |
| Gly | Leu | Met | Ala | Ala | Thr | Gly | Ile | Leu | Lys | Gly | Met | Leu | Ala | Leu | Ala | |
| | | 115 | | | | | 120 | | | | | 125 | | | | |
| ctc | act | ttt | cag | tgg | acg | acc | gaa | caa | agt | ggt | act | tat | tta | att | tta | 432 |
| Leu | Thr | Phe | Gln | Trp | Thr | Thr | Glu | Gln | Ser | Gly | Thr | Tyr | Leu | Ile | Leu | |
| | 130 | | | | | 135 | | | | | 140 | | | | | |
| ttc | agc | gcc | agt | gat | gcc | ttg | ttt | tgg | ttc | ttc | ccg | ata | atc | ctg | gga | 480 |
| Phe | Ser | Ala | Ser | Asp | Ala | Leu | Phe | Trp | Phe | Phe | Pro | Ile | Ile | Leu | Gly | |
| 145 | | | | 150 | | | | | 155 | | | | | 160 | | |
| tac | acc | gcg | ggg | aaa | cgc | ttc | ggc | ggt | aat | cca | ttt | act | gcc | atg | gtg | 528 |
| Tyr | Thr | Ala | Gly | Lys | Arg | Phe | Gly | Gly | Asn | Pro | Phe | Thr | Ala | Met | Val | |
| | | | 165 | | | | | 170 | | | | | 175 | | | |
| att | ggt | gga | gcg | tta | gtg | cat | cca | tta | att | ctg | act | gct | ttc | gag | aac | 576 |
| Ile | Gly | Gly | Ala | Leu | Val | His | Pro | Leu | Ile | Leu | Thr | Ala | Phe | Glu | Asn | |
| | | 180 | | | | | 185 | | | | | 190 | | | | |
| ggg | caa | aaa | gcg | gat | gcg | ctg | ggg | ctg | gat | ttc | ctg | ggt | att | ccg | gtc | 624 |
| Gly | Gln | Lys | Ala | Asp | Ala | Leu | Gly | Leu | Asp | Phe | Leu | Gly | Ile | Pro | Val | |
| | 195 | | | | | 200 | | | | | 205 | | | | | |
| aca | ttg | ttg | aat | tac | tcg | tca | tcg | gtt | att | ccc | att | att | ttt | tct | gcc | 672 |
| Thr | Leu | Leu | Asn | Tyr | Ser | Ser | Ser | Val | Ile | Pro | Ile | Ile | Phe | Ser | Ala | |
| 210 | | | | | 215 | | | | | 220 | | | | | | |
| tgg | ttg | tgc | agc | att | ctg | gaa | cgc | cga | ctt | aat | gcg | tgg | tta | ccg | tcg | 720 |
| Trp | Leu | Cys | Ser | Ile | Leu | Glu | Arg | Arg | Leu | Asn | Ala | Trp | Leu | Pro | Ser | |
| 225 | | | | | 230 | | | | | 235 | | | | | 240 | |
| gca | atc | aaa | aat | ttc | ttc | aca | cca | ttg | cta | tgt | ctg | atg | gtt | atc | aca | 768 |
| Ala | Ile | Lys | Asn | Phe | Phe | Thr | Pro | Leu | Leu | Cys | Leu | Met | Val | Ile | Thr | |
| | | | | 245 | | | | | 250 | | | | | 255 | | |
| ccc | gtc | acc | ttt | ctg | ctg | gtg | ggg | ccg | cta | tca | acc | tgg | ata | agc | gaa | 816 |
| Pro | Val | Thr | Phe | Leu | Leu | Val | Gly | Pro | Leu | Ser | Thr | Trp | Ile | Ser | Glu | |
| | | | 260 | | | | | 265 | | | | | 270 | | | |
| ctg | att | gcc | gcc | ggt | tat | ctc | tgg | ctt | tat | cag | gcg | gtt | cct | gca | ttt | 864 |
| Leu | Ile | Ala | Ala | Gly | Tyr | Leu | Trp | Leu | Tyr | Gln | Ala | Val | Pro | Ala | Phe | |
| | | 275 | | | | | 280 | | | | | 285 | | | | |
| gcg | ggc | gcg | gta | atg | ggc | ggc | ttc | tgg | caa | atc | ttc | gtc | atg | ttc | gga | 912 |
| Ala | Gly | Ala | Val | Met | Gly | Gly | Phe | Trp | Gln | Ile | Phe | Val | Met | Phe | Gly | |
| | 290 | | | | | 295 | | | | | 300 | | | | | |
| ctg | cac | tgg | ggc | ctg | gtg | ccg | ctg | tgt | atc | aat | aac | ttc | acc | gtg | ctg | 960 |
| Leu | His | Trp | Gly | Leu | Val | Pro | Leu | Cys | Ile | Asn | Asn | Phe | Thr | Val | Leu | |
| 305 | | | | | 310 | | | | | 315 | | | | | 320 | |
| ggc | tac | gac | acc | atg | atc | ccg | ctg | tta | atg | ccc | gcc | att | atg | gcg | cag | 1008 |
| Gly | Tyr | Asp | Thr | Met | Ile | Pro | Leu | Leu | Met | Pro | Ala | Ile | Met | Ala | Gln | |
| | | | | 325 | | | | | 330 | | | | | 335 | | |
| gtc | ggg | gcg | gcg | ctc | ggc | gtc | ttc | ctc | tgc | gaa | cgc | gat | gcg | cag | aaa | 1056 |
| Val | Gly | Ala | Ala | Leu | Gly | Val | Phe | Leu | Cys | Glu | Arg | Asp | Ala | Gln | Lys | |
| | | | 340 | | | | | 345 | | | | | 350 | | | |
| aaa | gtg | gtg | gcg | gga | tca | gcg | gcg | ttg | acg | agt | ctg | ttt | ggt | atc | acc | 1104 |
| Lys | Val | Val | Ala | Gly | Ser | Ala | Ala | Leu | Thr | Ser | Leu | Phe | Gly | Ile | Thr | |
| | | 355 | | | | | 360 | | | | | 365 | | | | |
| gaa | cca | gcg | gta | tat | ggc | gtc | aac | ctg | ccg | cgt | aag | tac | ccc | ttt | gtt | 1152 |
| Glu | Pro | Ala | Val | Tyr | Gly | Val | Asn | Leu | Pro | Arg | Lys | Tyr | Pro | Phe | Val | |
| | 370 | | | | | 375 | | | | | 380 | | | | | |
| atc | gcc | tgt | atc | agt | ggg | gct | ttg | ggg | gcc | acc | att | att | ggc | tac | gcg | 1200 |
| Ile | Ala | Cys | Ile | Ser | Gly | Ala | Leu | Gly | Ala | Thr | Ile | Ile | Gly | Tyr | Ala | |
| 385 | | | | | 390 | | | | | 395 | | | | | 400 | |
| caa | acg | aaa | gtc | tac | tcc | ttt | ggt | ttg | cca | agt | att | ttc | acc | ttc | atg | 1248 |
| Gln | Thr | Lys | Val | Tyr | Ser | Phe | Gly | Leu | Pro | Ser | Ile | Phe | Thr | Phe | Met | |
| | | | | 405 | | | | | 410 | | | | | 415 | | |
| caa | acc | atc | ccg | tca | acg | gga | att | gat | ttc | acc | gtc | tgg | gcc | agc | gtt | 1296 |
| Gln | Thr | Ile | Pro | Ser | Thr | Gly | Ile | Asp | Phe | Thr | Val | Trp | Ala | Ser | Val | |
| | | | 420 | | | | | 425 | | | | | 430 | | | |

```
att ggc ggt gtc att gcc atc ggt tgc gca ttt gtc ggt acg gtg atg      1344
Ile Gly Gly Val Ile Ala Ile Gly Cys Ala Phe Val Gly Thr Val Met
            435                 440                 445 ctt cat ttc atc acc gct aaa cgt cag cca gcg cag ggt gcc ccg caa      1392
Leu His Phe Ile Thr Ala Lys Arg Gln Pro Ala Gln Gly Ala Pro Gln
    450                 455                 460 gag aaa aca cca gag gtt att aca cca cct gag cag ggc ggt atc tgt      1440
Glu Lys Thr Pro Glu Val Ile Thr Pro Pro Glu Gln Gly Gly Ile Cys
465                 470                 475                 480 tca ccg atg acg gga gag att gtg ccg ctc att cac gtc gct gat acc      1488
Ser Pro Met Thr Gly Glu Ile Val Pro Leu Ile His Val Ala Asp Thr
                485                 490                 495 acg ttt gcc agt ggc ctg ttg ggt aaa ggt att gcc att ctg ccc tcg      1536
Thr Phe Ala Ser Gly Leu Leu Gly Lys Gly Ile Ala Ile Leu Pro Ser
            500                 505                 510 gtt ggt gaa gtg cgt tct ccg gtt gcg ggt cga att gct tcg ttg ttc      1584
Val Gly Glu Val Arg Ser Pro Val Ala Gly Arg Ile Ala Ser Leu Phe
        515                 520                 525 gcc aca tta cac gcc att ggc att gag tca gat gat ggt gtg gag atc      1632
Ala Thr Leu His Ala Ile Gly Ile Glu Ser Asp Asp Gly Val Glu Ile
    530                 535                 540 ctg att cat gtc ggt atc gac acc gta aaa ctg gac ggc aaa ttc ttt      1680
Leu Ile His Val Gly Ile Asp Thr Val Lys Leu Asp Gly Lys Phe Phe
545                 550                 555                 560 tcc gct cac gtc aac gtg ggt gac aag gtc aat aca ggc gat cgg ctg      1728
Ser Ala His Val Asn Val Gly Asp Lys Val Asn Thr Gly Asp Arg Leu
                565                 570                 575 att tct ttt gat atc cct gct att cgc gag gcc gga ttt gat ctg acg      1776
Ile Ser Phe Asp Ile Pro Ala Ile Arg Glu Ala Gly Phe Asp Leu Thr
            580                 585                 590 acg ccg gta tta atc agt aat agc gat gat ttt acg gac gta tta ccc      1824
Thr Pro Val Leu Ile Ser Asn Ser Asp Asp Phe Thr Asp Val Leu Pro
        595                 600                 605 cac ggc acg gcg cag ata agc gca ggt gaa ccg ctg tta tcc atc att      1872
His Gly Thr Ala Gln Ile Ser Ala Gly Glu Pro Leu Leu Ser Ile Ile
    610                 615                 620 cgc taa                                                              1878
Arg
625

<210> SEQ ID NO 6
<211> LENGTH: 625
<212> TYPE: PRT
<213> ORGANISM: Escherichia coli

<400> SEQUENCE: 6

Met Thr Glu Leu Ala Arg Lys Ile Val Ala Gly Val Gly Gly Ala Asp
1               5                   10                  15

Asn Ile Val Ser Leu Met His Cys Ala Thr Arg Leu Arg Phe Lys Leu
            20                  25                  30

Lys Asp Glu Ser Lys Ala Gln Ala Glu Val Leu Lys Lys Thr Pro Gly
        35                  40                  45

Ile Ile Met Val Val Glu Ser Gly Gly Gln Phe Gln Val Val Ile Gly
    50                  55                  60

Asn His Val Ala Asp Val Phe Leu Ala Val Asn Ser Val Ala Gly Leu
65                  70                  75                  80

Asp Glu Lys Ala Gln Gln Ala Pro Glu Asn Asp Asp Lys Gly Asn Leu
                85                  90                  95

Leu Asn Arg Phe Val Tyr Val Ile Ser Gly Ile Phe Thr Pro Leu Ile
            100                 105                 110
```

```
Gly Leu Met Ala Ala Thr Gly Ile Leu Lys Gly Met Leu Ala Leu Ala
            115                 120                 125

Leu Thr Phe Gln Trp Thr Thr Glu Gln Ser Gly Thr Tyr Leu Ile Leu
130             135                 140

Phe Ser Ala Ser Asp Ala Leu Phe Trp Phe Pro Ile Ile Leu Gly
145                 150                 155                 160

Tyr Thr Ala Gly Lys Arg Phe Gly Gly Asn Pro Phe Thr Ala Met Val
                165                 170                 175

Ile Gly Gly Ala Leu Val His Pro Leu Ile Leu Thr Ala Phe Glu Asn
                180                 185                 190

Gly Gln Lys Ala Asp Ala Leu Gly Leu Asp Phe Leu Gly Ile Pro Val
            195                 200                 205

Thr Leu Leu Asn Tyr Ser Ser Ser Val Ile Pro Ile Ile Phe Ser Ala
210                 215                 220

Trp Leu Cys Ser Ile Leu Glu Arg Arg Leu Asn Ala Trp Leu Pro Ser
225                 230                 235                 240

Ala Ile Lys Asn Phe Phe Thr Pro Leu Leu Cys Leu Met Val Ile Thr
                245                 250                 255

Pro Val Thr Phe Leu Leu Val Gly Pro Leu Ser Thr Trp Ile Ser Glu
                260                 265                 270

Leu Ile Ala Ala Gly Tyr Leu Trp Leu Tyr Gln Ala Val Pro Ala Phe
            275                 280                 285

Ala Gly Ala Val Met Gly Gly Phe Trp Gln Ile Phe Val Met Phe Gly
            290                 295                 300

Leu His Trp Gly Leu Val Pro Leu Cys Ile Asn Asn Phe Thr Val Leu
305                 310                 315                 320

Gly Tyr Asp Thr Met Ile Pro Leu Leu Met Pro Ala Ile Met Ala Gln
                325                 330                 335

Val Gly Ala Ala Leu Gly Val Phe Leu Cys Glu Arg Asp Ala Gln Lys
            340                 345                 350

Lys Val Val Ala Gly Ser Ala Ala Leu Thr Ser Leu Phe Gly Ile Thr
            355                 360                 365

Glu Pro Ala Val Tyr Gly Val Asn Leu Pro Arg Lys Tyr Pro Phe Val
370                 375                 380

Ile Ala Cys Ile Ser Gly Ala Leu Gly Ala Thr Ile Ile Gly Tyr Ala
385                 390                 395                 400

Gln Thr Lys Val Tyr Ser Phe Gly Leu Pro Ser Ile Phe Thr Phe Met
                405                 410                 415

Gln Thr Ile Pro Ser Thr Gly Ile Asp Phe Thr Val Trp Ala Ser Val
            420                 425                 430

Ile Gly Gly Val Ile Ala Ile Gly Cys Ala Phe Val Gly Thr Val Met
            435                 440                 445

Leu His Phe Ile Thr Ala Lys Arg Gln Pro Ala Gln Gly Ala Pro Gln
450                 455                 460

Glu Lys Thr Pro Glu Val Ile Thr Pro Pro Glu Gln Gly Gly Ile Cys
465                 470                 475                 480

Ser Pro Met Thr Gly Glu Ile Val Pro Leu Ile His Val Ala Asp Thr
                485                 490                 495

Thr Phe Ala Ser Gly Leu Leu Gly Lys Gly Ile Ala Ile Leu Pro Ser
                500                 505                 510

Val Gly Glu Val Arg Ser Pro Val Ala Gly Arg Ile Ala Ser Leu Phe
            515                 520                 525

Ala Thr Leu His Ala Ile Gly Ile Glu Ser Asp Asp Gly Val Glu Ile
530                 535                 540
```

```
Leu Ile His Val Gly Ile Asp Thr Val Lys Leu Asp Gly Lys Phe Phe
545                 550                 555                 560

Ser Ala His Val Asn Val Gly Asp Lys Val Asn Thr Gly Asp Arg Leu
                565                 570                 575

Ile Ser Phe Asp Ile Pro Ala Ile Arg Glu Ala Gly Phe Asp Leu Thr
            580                 585                 590

Thr Pro Val Leu Ile Ser Asn Ser Asp Asp Phe Thr Asp Val Leu Pro
        595                 600                 605

His Gly Thr Ala Gln Ile Ser Ala Gly Glu Pro Leu Leu Ser Ile Ile
    610                 615                 620

Arg
625

<210> SEQ ID NO 7
<211> LENGTH: 1434
<212> TYPE: DNA
<213> ORGANISM: Escherichia coli
<220> FEATURE:
<221> NAME/KEY: CDS
<222> LOCATION: (1)..(1434)
<223> OTHER INFORMATION: ptsG

<400> SEQUENCE: 7 atg ttt aag aat gca ttt gct aac ctg caa aag gtc ggt aaa tcg ctg      48
Met Phe Lys Asn Ala Phe Ala Asn Leu Gln Lys Val Gly Lys Ser Leu
1               5                   10                  15 atg ctg ccg gta tcc gta ctg cct atc gca ggt att ctg ctg ggc gtc      96
Met Leu Pro Val Ser Val Leu Pro Ile Ala Gly Ile Leu Leu Gly Val
            20                  25                  30 ggt tcc gcg aat ttc agc tgg ctg ccc gcc gtt gta tcg cat gtt atg     144
Gly Ser Ala Asn Phe Ser Trp Leu Pro Ala Val Val Ser His Val Met
        35                  40                  45 gca gaa gca ggc ggt tcc gtc ttt gca aac atg cca ctg att ttt gcg     192
Ala Glu Ala Gly Gly Ser Val Phe Ala Asn Met Pro Leu Ile Phe Ala
    50                  55                  60 atc ggt gtc gcc ctc ggc ttt acc aat aac gat ggc gta tcc gcg ctg     240
Ile Gly Val Ala Leu Gly Phe Thr Asn Asn Asp Gly Val Ser Ala Leu
65                  70                  75                  80 gcc gca gtt gtt gcc tat ggc atc atg gtt aaa acc atg gcc gtg gtt     288
Ala Ala Val Val Ala Tyr Gly Ile Met Val Lys Thr Met Ala Val Val
                85                  90                  95 gcg cca ctg gta ctg cat tta cct gct gaa gaa atc gcc tct aaa cac     336
Ala Pro Leu Val Leu His Leu Pro Ala Glu Glu Ile Ala Ser Lys His
            100                 105                 110 ctg gcg gat act ggc gta ctc gga ggg att atc tcc ggt gcg atc gca     384
Leu Ala Asp Thr Gly Val Leu Gly Gly Ile Ile Ser Gly Ala Ile Ala
        115                 120                 125 gcg tac atg ttt aac cgt ttc tac cgt att aag ctg cct gag tat ctt     432
Ala Tyr Met Phe Asn Arg Phe Tyr Arg Ile Lys Leu Pro Glu Tyr Leu
    130                 135                 140 ggc ttc ttt gcc ggt aaa cgc ttt gtg ccg atc att tct ggc ctg gct     480
Gly Phe Phe Ala Gly Lys Arg Phe Val Pro Ile Ile Ser Gly Leu Ala
145                 150                 155                 160 gcc atc ttt act ggc gtt gtg ctg tcc ttc att tgg ccg ccg att ggt     528
Ala Ile Phe Thr Gly Val Val Leu Ser Phe Ile Trp Pro Pro Ile Gly
                165                 170                 175 tct gca atc cag acc ttc tct cag tgg gct gct tac cag aac ccg gta     576
Ser Ala Ile Gln Thr Phe Ser Gln Trp Ala Ala Tyr Gln Asn Pro Val
            180                 185                 190
```

| | | |
|---|---|---|
| gtt gcg ttt ggc att tac ggt ttc atc gaa cgt tgc ctg gta ccg ttt<br>Val Ala Phe Gly Ile Tyr Gly Phe Ile Glu Arg Cys Leu Val Pro Phe<br>195                            200                           205 | | 624 |
| ggt ctg cac cac atc tgg aac gta cct ttc cag atg cag att ggt gaa<br>Gly Leu His His Ile Trp Asn Val Pro Phe Gln Met Gln Ile Gly Glu<br>      210                        215                        220 | | 672 |
| tac acc aac gca gca ggt cag gtt ttc cac ggc gac att ccg cgt tat<br>Tyr Thr Asn Ala Ala Gly Gln Val Phe His Gly Asp Ile Pro Arg Tyr<br>225                          230                          235                240 | | 720 |
| atg gcg ggt gac ccg act gcg ggt aaa ctg tct ggt ggc ttc ctg ttc<br>Met Ala Gly Asp Pro Thr Ala Gly Lys Leu Ser Gly Gly Phe Leu Phe<br>               245                        250                        255 | | 768 |
| aaa atg tac ggt ctg cca gct gcc gca att gct atc tgg cac tct gct<br>Lys Met Tyr Gly Leu Pro Ala Ala Ala Ile Ala Ile Trp His Ser Ala<br>260                            265                          270 | | 816 |
| aaa cca gaa aac cgc gcg aaa gtg ggc ggt att atg atc tcc gcg gcg<br>Lys Pro Glu Asn Arg Ala Lys Val Gly Gly Ile Met Ile Ser Ala Ala<br>               275                        280                        285 | | 864 |
| ctg acc tcg ttc ctg acc ggt atc acc gag ccg atc gag ttc tcc ttc<br>Leu Thr Ser Phe Leu Thr Gly Ile Thr Glu Pro Ile Glu Phe Ser Phe<br>290                            295                          300 | | 912 |
| atg ttc gtt gcg ccg atc ctg tac atc atc cac gcg att ctg gca ggc<br>Met Phe Val Ala Pro Ile Leu Tyr Ile Ile His Ala Ile Leu Ala Gly<br>305                          310                          315                320 | | 960 |
| ctg gca ttc cca atc tgt att ctt ctg ggg atg cgt gac ggt acg tcg<br>Leu Ala Phe Pro Ile Cys Ile Leu Leu Gly Met Arg Asp Gly Thr Ser<br>               325                        330                        335 | | 1008 |
| ttc tcg cac ggt ctg atc gac ttc atc gtt ctg tct ggt aac agc agc<br>Phe Ser His Gly Leu Ile Asp Phe Ile Val Leu Ser Gly Asn Ser Ser<br>                    340                        345                        350 | | 1056 |
| aaa ctg tgg ctg ttc ccg atc gtc ggt atc ggt tat gcg att gtt tac<br>Lys Leu Trp Leu Phe Pro Ile Val Gly Ile Gly Tyr Ala Ile Val Tyr<br>      355                        360                        365 | | 1104 |
| tac acc atc ttc cgc gtg ctg att aaa gca ctg gat ctg aaa acg ccg<br>Tyr Thr Ile Phe Arg Val Leu Ile Lys Ala Leu Asp Leu Lys Thr Pro<br>370                          375                          380 | | 1152 |
| ggt cgt gaa gac gcg act gaa gat gca aaa gcg aca ggt acc agc gaa<br>Gly Arg Glu Asp Ala Thr Glu Asp Ala Lys Ala Thr Gly Thr Ser Glu<br>385                          390                        395                400 | | 1200 |
| atg gca ccg gct ctg gtt gct gca ttt ggt ggt aaa gaa aac att act<br>Met Ala Pro Ala Leu Val Ala Ala Phe Gly Gly Lys Glu Asn Ile Thr<br>                    405                        410                        415 | | 1248 |
| aac ctc gac gca tgt att acc cgt ctg cgc gtc agc gtt gct gat gtg<br>Asn Leu Asp Ala Cys Ile Thr Arg Leu Arg Val Ser Val Ala Asp Val<br>              420                        425                        430 | | 1296 |
| tct aaa gtg gat cag gcc ggc ctg aag aaa ctg ggc gca gcg ggc gta<br>Ser Lys Val Asp Gln Ala Gly Leu Lys Lys Leu Gly Ala Ala Gly Val<br>435                          440                          445 | | 1344 |
| gtg gtt gct ggt tct ggt gtt cag gcg att ttc ggt act aaa tcc gat<br>Val Val Ala Gly Ser Gly Val Gln Ala Ile Phe Gly Thr Lys Ser Asp<br>      450                        455                        460 | | 1392 |
| aac ctg aaa acc gag atg gat gag tac atc cgt aac cac taa<br>Asn Leu Lys Thr Glu Met Asp Glu Tyr Ile Arg Asn His<br>465                          470                        475 | | 1434 |

<210> SEQ ID NO 8
<211> LENGTH: 477
<212> TYPE: PRT
<213> ORGANISM: Escherichia coli

```
<400> SEQUENCE: 8

Met Phe Lys Asn Ala Phe Ala Asn Leu Gln Lys Val Gly Lys Ser Leu
1               5                   10                  15

Met Leu Pro Val Ser Val Leu Pro Ile Ala Gly Ile Leu Leu Gly Val
            20                  25                  30

Gly Ser Ala Asn Phe Ser Trp Leu Pro Ala Val Val Ser His Val Met
        35                  40                  45

Ala Glu Ala Gly Gly Ser Val Phe Ala Asn Met Pro Leu Ile Phe Ala
    50                  55                  60

Ile Gly Val Ala Leu Gly Phe Thr Asn Asn Asp Gly Val Ser Ala Leu
65                  70                  75                  80

Ala Ala Val Val Ala Tyr Gly Ile Met Val Lys Thr Met Ala Val Val
                85                  90                  95

Ala Pro Leu Val Leu His Leu Pro Ala Glu Glu Ile Ala Ser Lys His
            100                 105                 110

Leu Ala Asp Thr Gly Val Leu Gly Gly Ile Ile Ser Gly Ala Ile Ala
        115                 120                 125

Ala Tyr Met Phe Asn Arg Phe Tyr Arg Ile Lys Leu Pro Glu Tyr Leu
    130                 135                 140

Gly Phe Phe Ala Gly Lys Arg Phe Val Pro Ile Ile Ser Gly Leu Ala
145                 150                 155                 160

Ala Ile Phe Thr Gly Val Val Leu Ser Phe Ile Trp Pro Pro Ile Gly
                165                 170                 175

Ser Ala Ile Gln Thr Phe Ser Gln Trp Ala Ala Tyr Gln Asn Pro Val
            180                 185                 190

Val Ala Phe Gly Ile Tyr Gly Phe Ile Glu Arg Cys Leu Val Pro Phe
        195                 200                 205

Gly Leu His His Ile Trp Asn Val Pro Phe Gln Met Gln Ile Gly Glu
    210                 215                 220

Tyr Thr Asn Ala Ala Gly Gln Val Phe His Gly Asp Ile Pro Arg Tyr
225                 230                 235                 240

Met Ala Gly Asp Pro Thr Ala Gly Lys Leu Ser Gly Gly Phe Leu Phe
                245                 250                 255

Lys Met Tyr Gly Leu Pro Ala Ala Ala Ile Ala Ile Trp His Ser Ala
            260                 265                 270

Lys Pro Glu Asn Arg Ala Lys Val Gly Gly Ile Met Ile Ser Ala Ala
        275                 280                 285

Leu Thr Ser Phe Leu Thr Gly Ile Thr Glu Pro Ile Glu Phe Ser Phe
    290                 295                 300

Met Phe Val Ala Pro Ile Leu Tyr Ile Ile His Ala Ile Leu Ala Gly
305                 310                 315                 320

Leu Ala Phe Pro Ile Cys Ile Leu Leu Gly Met Arg Asp Gly Thr Ser
                325                 330                 335

Phe Ser His Gly Leu Ile Asp Phe Ile Val Leu Ser Gly Asn Ser Ser
            340                 345                 350

Lys Leu Trp Leu Phe Pro Ile Val Gly Ile Gly Tyr Ala Ile Val Tyr
        355                 360                 365

Tyr Thr Ile Phe Arg Val Leu Ile Lys Ala Leu Asp Leu Lys Thr Pro
    370                 375                 380

Gly Arg Glu Asp Ala Thr Glu Asp Ala Lys Ala Thr Gly Thr Ser Glu
385                 390                 395                 400

Met Ala Pro Ala Leu Val Ala Ala Phe Gly Gly Lys Glu Asn Ile Thr
                405                 410                 415
```

```
Asn Leu Asp Ala Cys Ile Thr Arg Leu Arg Val Ser Val Ala Asp Val
                420                 425                 430

Ser Lys Val Asp Gln Ala Gly Leu Lys Lys Leu Gly Ala Ala Gly Val
        435                 440                 445

Val Val Ala Gly Ser Gly Val Gln Ala Ile Phe Gly Thr Lys Ser Asp
    450                 455                 460

Asn Leu Lys Thr Glu Met Asp Glu Tyr Ile Arg Asn His
465                 470                 475

<210> SEQ ID NO 9
<211> LENGTH: 101
<212> TYPE: DNA
<213> ORGANISM: Artificial Sequence
<220> FEATURE:
<223> OTHER INFORMATION: lambda phage

<400> SEQUENCE: 9 cctgctttt  tatactaagt  tggcattata  aaaaagcatt  gcttatcaat  ttgttgcaac     60
gaacaggtca  ctatcagtca  aaataaaatc  attatttgat  t                       101

<210> SEQ ID NO 10
<211> LENGTH: 172
<212> TYPE: DNA
<213> ORGANISM: Artificial Sequence
<220> FEATURE:
<223> OTHER INFORMATION: lambda phage

<400> SEQUENCE: 10
gcgctaatgc  tctgttacag  gtcactaata  ccatctaagt  agttgattca  tagtgactgc     60
atatgttgtg  ttttacagta  ttatgtagtc  tgttttttat  gcaaaatcta  atttaatata    120
ttgatattta  tcattttta   cgtttctcgt  tcagcttttt  tatactaact  tg            172

<210> SEQ ID NO 11
<211> LENGTH: 120
<212> TYPE: DNA
<213> ORGANISM: Artificial Sequence
<220> FEATURE:
<223> OTHER INFORMATION: lambda phage

<400> SEQUENCE: 11
agatcttgaa  gcctgctttt  ttatactaag  ttggcattat  aaaaaagcat  tgcttatcaa     60
tttgttgcaa  cgaacaggtc  actatcagtc  aaaataaaat  cattatttga  tttcgaattc    120

<210> SEQ ID NO 12
<211> LENGTH: 184
<212> TYPE: DNA
<213> ORGANISM: Artificial Sequence
<220> FEATURE:
<223> OTHER INFORMATION: lambda phage

<400> SEQUENCE: 12
ctgcagtctg  ttacaggtca  ctaataccat  ctaagtagtt  gattcatagt  gactgcatat     60
gttgtgtttt  acagtattat  gtagtctgtt  ttttatgcaa  aatctaattt  aatatattga    120
tatttatatc  attttacgtt  tctcgttcag  cttttttata  ctaacttgag  cgtctagaaa    180
gctt                                                                    184

<210> SEQ ID NO 13
<211> LENGTH: 1071
<212> TYPE: DNA
<213> ORGANISM: Artificial Sequence
```

```
<220> FEATURE:
<221> NAME/KEY: CDS
<222> LOCATION: (1)..(1071)
<223> OTHER INFORMATION: lambda phage

<400> SEQUENCE: 13 atg gga aga agg cga agt cat gag cgc cgg gat tta ccc cct aac ctt        48
Met Gly Arg Arg Arg Ser His Glu Arg Arg Asp Leu Pro Pro Asn Leu
1               5                   10                  15 tat ata aga aac aat gga tat tac tgc tac agg gac cca agg acg ggt        96
Tyr Ile Arg Asn Asn Gly Tyr Tyr Cys Tyr Arg Asp Pro Arg Thr Gly
                20                  25                  30 aaa gag ttt gga tta ggc aga gac agg cga atc gca atc act gaa gct       144
Lys Glu Phe Gly Leu Gly Arg Asp Arg Arg Ile Ala Ile Thr Glu Ala
            35                  40                  45 ata cag gcc aac att gag tta ttt tca gga cac aaa cac aag cct ctg       192
Ile Gln Ala Asn Ile Glu Leu Phe Ser Gly His Lys His Lys Pro Leu
        50                  55                  60 aca gcg aga atc aac agt gat aat tcc gtt acg tta cat tca tgg ctt       240
Thr Ala Arg Ile Asn Ser Asp Asn Ser Val Thr Leu His Ser Trp Leu
65                  70                  75                  80 gat cgc tac gaa aaa atc ctg gcc agc aga gga atc aag cag aag aca       288
Asp Arg Tyr Glu Lys Ile Leu Ala Ser Arg Gly Ile Lys Gln Lys Thr
                85                  90                  95 ctc ata aat tac atg agc aaa att aaa gca ata agg agg ggt ctg cct       336
Leu Ile Asn Tyr Met Ser Lys Ile Lys Ala Ile Arg Arg Gly Leu Pro
            100                 105                 110 gat gct cca ctt gaa gac atc acc aca aaa gaa att gcg gca atg ctc       384
Asp Ala Pro Leu Glu Asp Ile Thr Thr Lys Glu Ile Ala Ala Met Leu
        115                 120                 125 aat gga tac ata gac gag ggc aag gcg gcg tca gcc aag tta atc aga       432
Asn Gly Tyr Ile Asp Glu Gly Lys Ala Ala Ser Ala Lys Leu Ile Arg
    130                 135                 140 tca aca ctg agc gat gca ttc cga gag gca ata gct gaa ggc cat ata       480
Ser Thr Leu Ser Asp Ala Phe Arg Glu Ala Ile Ala Glu Gly His Ile
145                 150                 155                 160 aca aca aac cat gtc gct gcc act cgc gca gca aaa tca gag gta agg       528
Thr Thr Asn His Val Ala Ala Thr Arg Ala Ala Lys Ser Glu Val Arg
                165                 170                 175 aga tca aga ctt acg gct gac gaa tac ctg aaa att tat caa gca gca       576
Arg Ser Arg Leu Thr Ala Asp Glu Tyr Leu Lys Ile Tyr Gln Ala Ala
            180                 185                 190 gaa tca tca cca tgt tgg ctc aga ctt gca atg gaa ctg gct gtt gtt       624
Glu Ser Ser Pro Cys Trp Leu Arg Leu Ala Met Glu Leu Ala Val Val
        195                 200                 205 acc ggg caa cga gtt ggt gat tta tgc gaa atg aag tgg tct gat atc       672
Thr Gly Gln Arg Val Gly Asp Leu Cys Glu Met Lys Trp Ser Asp Ile
    210                 215                 220 gta gat gga tat ctt tat gtc gag caa agc aaa aca ggc gta aaa att       720
Val Asp Gly Tyr Leu Tyr Val Glu Gln Ser Lys Thr Gly Val Lys Ile
225                 230                 235                 240 gcc atc cca aca gca ttg cat att gat gct ctc gga ata tca atg aag       768
Ala Ile Pro Thr Ala Leu His Ile Asp Ala Leu Gly Ile Ser Met Lys
                245                 250                 255 gaa aca ctt gat aaa tgc aaa gag att ctt ggc gga gaa acc ata att       816
Glu Thr Leu Asp Lys Cys Lys Glu Ile Leu Gly Gly Glu Thr Ile Ile
            260                 265                 270 gca tct act cgt cgc gaa ccg ctt tca tcc ggc aca gta tca agg tat       864
Ala Ser Thr Arg Arg Glu Pro Leu Ser Ser Gly Thr Val Ser Arg Tyr
        275                 280                 285
```

```
ttt atg cgc gca cga aaa gca tca ggt ctt tcc ttc gaa ggg gat ccg    912
Phe Met Arg Ala Arg Lys Ala Ser Gly Leu Ser Phe Glu Gly Asp Pro
    290                 295                 300 cct acc ttt cac gag ttg cgc agt ttg tct gca aga ctc tat gag aag    960
Pro Thr Phe His Glu Leu Arg Ser Leu Ser Ala Arg Leu Tyr Glu Lys
305                 310                 315                 320 cag ata agc gat aag ttt gct caa cat ctt ctc ggg cat aag tcg gac   1008
Gln Ile Ser Asp Lys Phe Ala Gln His Leu Leu Gly His Lys Ser Asp
                325                 330                 335 acc atg gca tca cag tat cgt gat gac aga ggc agg gag tgg gac aaa   1056
Thr Met Ala Ser Gln Tyr Arg Asp Asp Arg Gly Arg Glu Trp Asp Lys
            340                 345                 350 att gaa atc aaa taa                                                1071
Ile Glu Ile Lys
355

<210> SEQ ID NO 14
<211> LENGTH: 356
<212> TYPE: PRT
<213> ORGANISM: Artificial Sequence
<220> FEATURE:
<223> OTHER INFORMATION: lambda phage

<400> SEQUENCE: 14

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Glu Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Glu Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270
```

```
Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
        290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
        355

<210> SEQ ID NO 15
<211> LENGTH: 219
<212> TYPE: DNA
<213> ORGANISM: Artificial Sequence
<220> FEATURE:
<221> NAME/KEY: CDS
<222> LOCATION: (1)..(219)
<223> OTHER INFORMATION: lambda phage

<400> SEQUENCE: 15 atg tac ttg aca ctt cag gag tgg aac gca cgc cag cga cgt cca aga    48
Met Tyr Leu Thr Leu Gln Glu Trp Asn Ala Arg Gln Arg Arg Pro Arg
1               5                  10                  15 agc ctt gaa aca gtt cgt cga tgg gtt cgg gaa tgc agg ata ttc cca    96
Ser Leu Glu Thr Val Arg Arg Trp Val Arg Glu Cys Arg Ile Phe Pro
            20                  25                  30 cct ccg gtt aag gat gga aga gag tat ctg ttc cac gaa tca gcg gta   144
Pro Pro Val Lys Asp Gly Arg Glu Tyr Leu Phe His Glu Ser Ala Val
        35                  40                  45 aag gtt gac tta aat cga cca gta aca ggt ggc ctt ttg aag agg atc   192
Lys Val Asp Leu Asn Arg Pro Val Thr Gly Gly Leu Leu Lys Arg Ile
    50                  55                  60 aga aat ggg aag aag gcg aag tca tga                               219
Arg Asn Gly Lys Lys Ala Lys Ser
65                  70

<210> SEQ ID NO 16
<211> LENGTH: 72
<212> TYPE: PRT
<213> ORGANISM: Artificial Sequence
<220> FEATURE:
<223> OTHER INFORMATION: lambda phage

<400> SEQUENCE: 16

Met Tyr Leu Thr Leu Gln Glu Trp Asn Ala Arg Gln Arg Arg Pro Arg
1               5                  10                  15

Ser Leu Glu Thr Val Arg Arg Trp Val Arg Glu Cys Arg Ile Phe Pro
            20                  25                  30

Pro Pro Val Lys Asp Gly Arg Glu Tyr Leu Phe His Glu Ser Ala Val
        35                  40                  45

Lys Val Asp Leu Asn Arg Pro Val Thr Gly Gly Leu Leu Lys Arg Ile
    50                  55                  60

Arg Asn Gly Lys Lys Ala Lys Ser
65                  70

<210> SEQ ID NO 17
<211> LENGTH: 40
<212> TYPE: DNA
<213> ORGANISM: Artificial Sequence
```

```
<220> FEATURE:
<223> OTHER INFORMATION: oligonucleotide P1

<400> SEQUENCE: 17
ctagtaagat cttgaagcct gcttttttat actaagttgg                    40

<210> SEQ ID NO 18
<211> LENGTH: 41
<212> TYPE: DNA
<213> ORGANISM: Artificial Sequence
<220> FEATURE:
<223> OTHER INFORMATION: oligonucleotide P2

<400> SEQUENCE: 18
atgatcgaat tcgaaatcaa ataatgattt tattttgact g                  41

<210> SEQ ID NO 19
<211> LENGTH: 41
<212> TYPE: DNA
<213> ORGANISM: Artificial Sequence
<220> FEATURE:
<223> OTHER INFORMATION: oligonucleotide P3

<400> SEQUENCE: 19
atgccactgc agtctgttac aggtcactaa taccatctaa g                  41

<210> SEQ ID NO 20
<211> LENGTH: 46
<212> TYPE: DNA
<213> ORGANISM: Artificial Sequence
<220> FEATURE:
<223> OTHER INFORMATION: oligonucleotide P4

<400> SEQUENCE: 20
accgttaagc tttctagacg ctcaagttag tataaaaaag ctgaac             46

<210> SEQ ID NO 21
<211> LENGTH: 38
<212> TYPE: DNA
<213> ORGANISM: Artificial Sequence
<220> FEATURE:
<223> OTHER INFORMATION: oligonucleotide P5

<400> SEQUENCE: 21
ttcttagacg tcaggtggca cttttcgggg aaatgtgc                      38

<210> SEQ ID NO 22
<211> LENGTH: 37
<212> TYPE: DNA
<213> ORGANISM: Artificial Sequence
<220> FEATURE:
<223> OTHER INFORMATION: oligonucleotide P6

<400> SEQUENCE: 22
taacagagat ctcgcgcaga aaaaaggat ctcaaga                        37

<210> SEQ ID NO 23
<211> LENGTH: 46
<212> TYPE: DNA
<213> ORGANISM: Artificial Sequence
<220> FEATURE:
<223> OTHER INFORMATION: oligonucleotide P7

<400> SEQUENCE: 23
aacagagatc taagcttaga tcctttgcct ggcggcagta gcgcgg             46
```

```
<210> SEQ ID NO 24
<211> LENGTH: 35
<212> TYPE: DNA
<213> ORGANISM: Artificial Sequence
<220> FEATURE:
<223> OTHER INFORMATION: oligonucleotide P8

<400> SEQUENCE: 24
ataaactgca gcaaaaagag tttgtagaaa cgcaa                               35

<210> SEQ ID NO 25
<211> LENGTH: 36
<212> TYPE: DNA
<213> ORGANISM: Artificial Sequence
<220> FEATURE:
<223> OTHER INFORMATION: oligonucleotide P9

<400> SEQUENCE: 25
agtaattcta gaaagcttaa cacagaaaaa agcccg                              36

<210> SEQ ID NO 26
<211> LENGTH: 43
<212> TYPE: DNA
<213> ORGANISM: Artificial Sequence
<220> FEATURE:
<223> OTHER INFORMATION: oligonucleotide P10

<400> SEQUENCE: 26
ctagtaggat ccctgcagtg gtcgaaaaaa aaagcccgca ctg                      43

<210> SEQ ID NO 27
<211> LENGTH: 37
<212> TYPE: DNA
<213> ORGANISM: Artificial Sequence
<220> FEATURE:
<223> OTHER INFORMATION: oligonucleotide P11

<400> SEQUENCE: 27
atcgaggtac cagatctccg gataagtaga cagcctg                             37

<210> SEQ ID NO 28
<211> LENGTH: 32
<212> TYPE: DNA
<213> ORGANISM: Artificial Sequence
<220> FEATURE:
<223> OTHER INFORMATION: oligonucleotide P12

<400> SEQUENCE: 28
gaaggtctag agcgcccggt tgacgctgct ag                                  32

<210> SEQ ID NO 29
<211> LENGTH: 1388
<212> TYPE: DNA
<213> ORGANISM: Artificial Sequence
<220> FEATURE:
<223> OTHER INFORMATION: cloned DNA fragment EcoRI-PstI including gene
      for tetracycline resistance (small EcoRI-Van91I fragment of
      pBR322) and transcription terminator ter_thrL

<400> SEQUENCE: 29
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120
cggcaccgtc acctggatg ctgtaggcat aggcttggtt atgccggtac tgccgggcct   180
cttgcgggat atcgtccatt ccgacagcat cgccagtcac tatggcgtgc tgctagcgct   240
atatgcgttg atgcaatttc tatgcgcacc cgttctcgga gcactgtccg accgctttgg   300
```

```
ccgccgccca gtcctgctcg cttcgctact tggagccact atcgactacg cgatcatggc    360
gaccacaccc gtcctgtgga tcctctacgc cggacgcatc gtggccggca tcaccggcgc    420
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt gcggcggcgg tgctcaacgg    600
cctcaaccta ctactgggct gcttcctaat gcaggagtcg cataagggag agcgtcgacc    660
gatgcccttg agagccttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt cgctggagc gcgacgatga tcggcctgtc    840
gcttgcggta ttcggaatct gcacgcccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc   1020
ttccggcggc atcgggatgc ccgcgttgca ggccatgctg tccaggcagg tagatgacga   1080
ccatcaggga cagcttcaag gatcgctcgc ggctcttacc agcctaactt cgatcactgg   1140
accgctgatc gtcacggcga tttatgccgc ctcggcgagc acatggaacg ggttggcatg   1200
gattgtaggc gccgccctat accttgtctg cctccccgcg ttgcgtcgcg gtgcatggag   1260
ccgggccacc tcgacctgaa tggaagccgg cggcacctcg ctaacggatt caccactcca   1320
actagaaagc ttaacacaga aaaagcccg cacctgacag tgcgggcttt ttttttcgac    1380
cactgcag                                                            1388
```

<210> SEQ ID NO 30
<211> LENGTH: 1162
<212> TYPE: DNA
<213> ORGANISM: Artificial Sequence
<220> FEATURE:
<223> OTHER INFORMATION: cloned DNA fragment containing Artificial
Sequence DNA fragment including promoter PA2 (early promoter of
phage T7), cat gene for chloramphenicol resistance (CmR),
transcription terminator ter_thrL and attR

<400> SEQUENCE: 30

```
agatctccgg ataagtagac agcctgataa gtcgcacgaa aaacaggtat tgacaacatg     60
aagtaacatg cagtaagata caaatcgcta ggtaacacta gcagcgtcaa ccgggcgctc   120
tagctagagc caagctagct tggccggatc cgagattttc aggagctaag gaagctaaaa   180
tggagaaaaa aatcactgga tataccaccg ttgatatatc ccaatggcat cgtaaagaac   240
attttgaggc atttcagtca gttgctcaat gtacctataa ccagaccgtt cagctggata   300
ttacggcctt tttaaagacc gtaaagaaaa ataagcacaa gttttatccg gcctttattc   360
acattcttgc ccgcctgatg aatgctcatc cggaattccg tatggcaatg aaagacggtg   420
agctggtgat atgggatagt gttcaccctt gttacaccgt tttccatgag caaactgaaa   480
cgttttcatc gctctggagt gaataccacg acgatttccg gcagtttcta cacatatatt   540
cgcaagatgt ggcgtgttac ggtgaaaacc tggcctattt ccctaaaggg tttattgaga   600
atatgttttt cgtctcagcc aatccctggg tgagtttcac cagttttgat ttaaacgtgg   660
ccaatatgga caacttcttc gcccccgttt tcaccatggg caaatattat acgcaaggcg   720
acaaggtgct gatgccgctg gcgattcagg ttcatcatgc cgtctgtgat ggcttccatg   780
tcggcagaat gcttaatgaa ttacaacagt actgcgatga gtggcagggc ggggcgtaat   840 tttttttaagg cagttattgg tgcccttaaa cgcctggtgc tacgcctgaa taagtgataa   900
```

```
taagcggatg aatggcagaa attcgtcgaa gcttaacaca gaaaaaagcc cgcacctgac    960
agtgcgggct ttttttttcg accactgcag tctgttacag gtcactaata ccatctaagt   1020
agttgattca tagtgactgc atatgttgtg ttttacagta ttatgtagtc tgttttttat   1080
gcaaaatcta atttaatata ttgatattta tatcatttta cgtttctcgt tcagcttttt   1140
tatactaact tgagcgtcta ga                                            1162
```

```
<210> SEQ ID NO 31
<211> LENGTH: 27
<212> TYPE: DNA
<213> ORGANISM: Artificial Sequence
<220> FEATURE:
<223> OTHER INFORMATION: oligonucleotide P1'

<400> SEQUENCE: 31
ctaatatcga tgaagattct tgctcaa                                         27

<210> SEQ ID NO 32
<211> LENGTH: 34
<212> TYPE: DNA
<213> ORGANISM: Artificial Sequence
<220> FEATURE:
<223> OTHER INFORMATION: oligonucleotide P2'

<400> SEQUENCE: 32
gcgttgaatt ccatacaacc tccttagtac atgc                                 34

<210> SEQ ID NO 33
<211> LENGTH: 34
<212> TYPE: DNA
<213> ORGANISM: Artificial Sequence
<220> FEATURE:
<223> OTHER INFORMATION: oligonucleotide P3'

<400> SEQUENCE: 33
gtactagaat tcgtgtaatt gcggagactt tgcg                                 34

<210> SEQ ID NO 34
<211> LENGTH: 41
<212> TYPE: DNA
<213> ORGANISM: Artificial Sequence
<220> FEATURE:
<223> OTHER INFORMATION: oligonucleotide P4'

<400> SEQUENCE: 34
aatagcctgc agttatttga tttcaatttt gtcccactcc c                         41

<210> SEQ ID NO 35
<211> LENGTH: 38
<212> TYPE: DNA
<213> ORGANISM: Artificial Sequence
<220> FEATURE:
<223> OTHER INFORMATION: oligonucleotide P5'

<400> SEQUENCE: 35
ttcttagacg tcaggtggca cttttcgggg aaatgtgc                             38

<210> SEQ ID NO 36
<211> LENGTH: 37
<212> TYPE: DNA
<213> ORGANISM: Artificial Sequence
<220> FEATURE:
<223> OTHER INFORMATION: oligonucleotide P6'
```

```
<400> SEQUENCE: 36
taacagagat ctagcgcaga aaaaaaggat ctcaaga                                    37

<210> SEQ ID NO 37
<211> LENGTH: 35
<212> TYPE: DNA
<213> ORGANISM: Artificial Sequence
<220> FEATURE:
<223> OTHER INFORMATION: oligonucleotide P7'

<400> SEQUENCE: 37
ataaactgca gcaaaaagag tttgtagaaa cgcaa                                      35

<210> SEQ ID NO 38
<211> LENGTH: 34
<212> TYPE: DNA
<213> ORGANISM: Artificial Sequence
<220> FEATURE:
<223> OTHER INFORMATION: oligonucleotide P8'

<400> SEQUENCE: 38
aacagaagct ttttgcctgg cggcagtagc gcgg                                       34

<210> SEQ ID NO 39
<211> LENGTH: 879
<212> TYPE: DNA
<213> ORGANISM: Artificial Sequence
<220> FEATURE:
<223> OTHER INFORMATION: cloned DNA fragment containing cI repressor
      gene and promoter regions

<400> SEQUENCE: 39
tcgatgaaga ttcttgctca attgttatca gctatgcgcc gaccagaaca ccttgccgat           60
cagccaaacg tctcttcagg ccactgacta gcgataactt tccccacaac ggaacaactc          120
tcattgcatg ggatcattgg gtactgtggg tttagtggtt gtaaaaacac ctgaccgcta          180
tccctgatca gtttcttgaa ggtaaactca tcacccccaa gtctggctat gcagaaatca          240
cctggctcaa cagcctgctc agggtcaacg agaattaaca ttccgtcagg aaagcttggc          300
ttggagcctg ttggtgcggt catggaatta ccttcaacct caagccagaa tgcagaatca          360
ctggcttttt tggttgtgct tacccatctc tccgcatcac cttttggtaaa ggttctaagc         420 tcaggtgaga acatccctgc ctgaacatga gaaaaaacag ggtactcata ctcacttcta          480
agtgacggct gcatactaac cgcttcatac atctcgtaga tttctctggc gattgaaggg          540
ctaaattctt caacgctaac tttgagaatt tttgcaagca atgcggcgtt ataagcattt          600
aatgcattga tgccattaaa taaagcacca acgcctgact gccccatccc catcttgtct          660
gcgacagatt cctgggataa gccaagttca ttttttcttt tttcataaat tgctttaagg          720
cgacgtgcgt cctcaagctg ctcttgtgtt aatggtttct ttttttgtgct catacgttaa         780 atctatcacc gcaagggata aatatctaac accgtgcgtg ttgactattt tacctctggc          840
ggtgataatg gttgcatgta ctaaggaggt tgtatggaa                                 879

<210> SEQ ID NO 40
<211> LENGTH: 1290
<212> TYPE: DNA
<213> ORGANISM: Artificial Sequence
<220> FEATURE:
<223> OTHER INFORMATION: cloned DNA fragment containing int-xis genes
```

<400> SEQUENCE: 40

```
attatttgat tcaattttg tcccactccc tgcctctgtc atcacgatac tgtgatgcca    60
tggtgtccga cttatgcccg agaagatgtt gagcaaactt atcgcttatc tgcttctcat   120
agagtcttgc agacaaactg cgcaactcgt gaaaggtagg cggatcccct tcgaaggaaa   180
gacctgatgc ttttcgtgcg cgcataaaat accttgatac tgtgccggat gaaagcggtt   240
cgcgacgagt agatgcaatt atggtttctc cgccaagaat ctctttgcat ttatcaagtg   300
tttccttcat tgatattccg agagcatcaa tatgcaatgc tgttgggatg caattttta   360
cgcctgtttt gctttgctcg acataaagat atccatctac gatatcagac cacttcattt   420
cgcataaatc accaactcgt tgcccggtaa caacagccag ttccattgca agtctgagcc   480
aacatggtga tgattctgct gcttgataaa ttttcaggta ttcgtcagcc gtaagtcttg   540
atctccttac ctctgatttt gctgcgcgag tggcagcgac atggtttgtt gttatatggc   600
cttcagctat tgcctctcgg aatgcatcgc tcagtgttga tctgattaac ttggctgacg   660
ccgccttgcc ctcgtctatg tatccattga gcattgccgc aatttctttt gtggtgatgt   720
cttcaagtgg agcatcaggc agaccccctcc ttattgcttt aattttgctc atgtaattta   780
tgagtgtctt ctgcttgatt cctctgctgg ccaggatttt ttcgtagcga tcaagccatg   840
aatgtaacgt aacggaatta tcactgttga ttctcgctgt cagaggcttg tgtttgtgtc   900
ctgaaaataa ctcaatgttg gcctgtatag cttcagtgat tgcgattcgc ctgtctctgc   960
ctaatccaaa ctctttaccc gtccttgggt ccctgtagca gtaatatcca ttgtttctta  1020
tataaaggtt aggggtaaa tcccggcgct catgacttcg ccttcttccc atttctgatc   1080
ctcttcaaaa ggccacctgt tactggtcga tttaagtcaa cctttaccgc tgattcgtgg  1140
aacagatact ctcttccatc cttaaccgga ggtgggaata tcctgcattc ccgaacccat  1200
cgacgaactg tttcaaggct tcttggacgt cgctggcgtg cgttccactc ctgaagtgtc  1260
aagtacatcg caaagtctcc gcaattacac                                    1290
```

<210> SEQ ID NO 41
<211> LENGTH: 351
<212> TYPE: DNA
<213> ORGANISM: Artificial Sequence
<220> FEATURE:
<223> OTHER INFORMATION: ter_rrnB fragment (complement)

<400> SEQUENCE: 41

```
caaaaagagt ttgtagaaac gcaaaaaggc catccgtcag gatggccttc tgcttaattt    60
gatgcctggc agtttatggc gggcgtcctg cccgccaccc tccgggccgt tgcttcgcaa   120
cgttcaaatc cgctcccggc ggatttgtcc tactcaggag agcgttcacc gacaaacaac   180
agataaaacg aaaggcccag tctttcgact gagcctttcg ttttatttga tgcctggcag   240
ttccctactc tcgcatgggg agaccccaca ctaccatcgg cgctacggcg tttcacttct   300
gagttcggca tggggtcagg tgggaccacc gcgctactgc cgccaggcaa a            351
```

<210> SEQ ID NO 42
<211> LENGTH: 2148
<212> TYPE: DNA
<213> ORGANISM: Escherichia coli
<220> FEATURE:
<221> NAME/KEY: CDS
<222> LOCATION: (1)..(2148)

<400> SEQUENCE: 42

```
atg aac gtt att gca ata ttg aat cac atg ggg gtt tat ttt aaa gaa         48
Met Asn Val Ile Ala Ile Leu Asn His Met Gly Val Tyr Phe Lys Glu
1               5                   10                  15 gaa ccc atc cgt gaa ctt cat cgc gcg ctt gaa cgt ctg aac ttc cag         96
Glu Pro Ile Arg Glu Leu His Arg Ala Leu Glu Arg Leu Asn Phe Gln
                20                  25                  30 att gtt tac ccg aac gac cgt gac gac tta tta aaa ctg atc gaa aac        144
Ile Val Tyr Pro Asn Asp Arg Asp Asp Leu Leu Lys Leu Ile Glu Asn
            35                  40                  45 aat gcg cgt ctg tgc ggc gtt att ttt gac tgg gat aaa tat aat ctc        192
Asn Ala Arg Leu Cys Gly Val Ile Phe Asp Trp Asp Lys Tyr Asn Leu
        50                  55                  60 gag ctg tgc gaa gaa att agc aaa atg aac gag aac ctg ccg ttg tac        240
Glu Leu Cys Glu Glu Ile Ser Lys Met Asn Glu Asn Leu Pro Leu Tyr
65                  70                  75                  80 gcg ttc gct aat acg tat tcc act ctc gat gta agc ctg aat gac ctg        288
Ala Phe Ala Asn Thr Tyr Ser Thr Leu Asp Val Ser Leu Asn Asp Leu
                85                  90                  95 cgt tta cag att agc ttc ttt gaa tat gcg ctg ggt gct gct gaa gat        336
Arg Leu Gln Ile Ser Phe Phe Glu Tyr Ala Leu Gly Ala Ala Glu Asp
            100                 105                 110 att gct aat aag atc aag cag acc act gac gaa tat atc aac act att        384
Ile Ala Asn Lys Ile Lys Gln Thr Thr Asp Glu Tyr Ile Asn Thr Ile
        115                 120                 125 ctg cct ccg ctg act aaa gca ctg ttt aaa tat gtt cgt gaa ggt aaa        432
Leu Pro Pro Leu Thr Lys Ala Leu Phe Lys Tyr Val Arg Glu Gly Lys
130                 135                 140 tat act ttc tgt act cct ggt cac atg ggc ggt act gca ttc cag aaa        480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg        528
Ser Pro Val Gly Ser Leu Phe Tyr Asp Phe Phe Gly Pro Asn Thr Met
                165                 170                 175 aaa tct gat att tcc att tca gta tct gaa ctg ggt tct ctg ctg gat        576
Lys Ser Asp Ile Ser Ile Ser Val Ser Glu Leu Gly Ser Leu Leu Asp
            180                 185                 190 cac agt ggt cca cac aaa gaa gca gaa cag tat atc gct cgc gtc ttt        624
His Ser Gly Pro His Lys Glu Ala Glu Gln Tyr Ile Ala Arg Val Phe
        195                 200                 205 aac gca gac cgc agc tac atg gtg acc aac ggt act tcc act gcg aac        672
Asn Ala Asp Arg Ser Tyr Met Val Thr Asn Gly Thr Ser Thr Ala Asn
210                 215                 220 aaa att gtt ggt atg tac tct gct cca gca ggc agc acc att ctg att        720
Lys Ile Val Gly Met Tyr Ser Ala Pro Ala Gly Ser Thr Ile Leu Ile
225                 230                 235                 240 gac cgt aac tgc cac aaa tcg ctg acc cac ctg atg atg atg agc gat        768
Asp Arg Asn Cys His Lys Ser Leu Thr His Leu Met Met Met Ser Asp
                245                 250                 255 gtt acg cca atc tat ttc cgc ccg acc cgt aac gct tac ggt att ctt        816
Val Thr Pro Ile Tyr Phe Arg Pro Thr Arg Asn Ala Tyr Gly Ile Leu
            260                 265                 270 ggt ggt atc cca cag agt gaa ttc cag cac gct acc att gct aag cgc        864
Gly Gly Ile Pro Gln Ser Glu Phe Gln His Ala Thr Ile Ala Lys Arg
        275                 280                 285 gtg aaa gaa aca cca aac gca acc tgg ccg gta cat gct gta att acc        912
Val Lys Glu Thr Pro Asn Ala Thr Trp Pro Val His Ala Val Ile Thr
290                 295                 300
```

```
aac tct acc tat gat ggt ctg ctg tac aac acc gac ttc atc aag aaa    960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac   1008
Thr Leu Asp Val Lys Ser Ile His Phe Asp Ser Ala Trp Val Pro Tyr
                325                 330                 335 acc aac ttc tca ccg att tac gaa ggt aaa tgc ggt atg agc ggt ggc   1056
Thr Asn Phe Ser Pro Ile Tyr Glu Gly Lys Cys Gly Met Ser Gly Gly
            340                 345                 350 cgt gta gaa ggg aaa gtg att tac gaa acc cag tcc act cac aaa ctg   1104
Arg Val Glu Gly Lys Val Ile Tyr Glu Thr Gln Ser Thr His Lys Leu
        355                 360                 365 ctg gcg gcg ttc tct cag gct tcc atg atc cac gtt aaa ggt gac gta   1152
Leu Ala Ala Phe Ser Gln Ala Ser Met Ile His Val Lys Gly Asp Val
    370                 375                 380 aac gaa gaa acc ttt aac gaa gcc tac atg atg cac acc acc act tct   1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg   1248
Pro His Tyr Gly Ile Val Ala Ser Thr Glu Thr Ala Ala Ala Met Met
                405                 410                 415 aaa ggc aat gca ggt aag cgt ctg atc aac ggt tct att gaa cgt gcg   1296
Lys Gly Asn Ala Gly Lys Arg Leu Ile Asn Gly Ser Ile Glu Arg Ala
            420                 425                 430 atc aaa ttc cgt aaa gag atc aaa cgt ctg aga acg gaa tct gat ggc   1344
Ile Lys Phe Arg Lys Glu Ile Lys Arg Leu Arg Thr Glu Ser Asp Gly
        435                 440                 445 tgg ttc ttt gat gta tgg cag ccg gat cat atc gat acg act gaa tgc   1392
Trp Phe Phe Asp Val Trp Gln Pro Asp His Ile Asp Thr Thr Glu Cys
    450                 455                 460 tgg ccg ctg cgt tct gac agc acc tgg cac ggc ttc aaa aac atc gat   1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg   1488
Asn Glu His Met Tyr Leu Asp Pro Ile Lys Val Thr Leu Leu Thr Pro
                485                 490                 495 ggg atg gaa aaa gac ggc acc atg agc gac ttt ggt att ccg gcc agc   1536
Gly Met Glu Lys Asp Gly Thr Met Ser Asp Phe Gly Ile Pro Ala Ser
            500                 505                 510 atc gtg gcg aaa tac ctc gac gaa cat ggc atc gtt gtt gag aaa acc   1584
Ile Val Ala Lys Tyr Leu Asp Glu His Gly Ile Val Val Glu Lys Thr
        515                 520                 525 ggt ccg tat aac ctg ctg ttc ctg ttc agc atc ggt atc gat aag acc   1632
Gly Pro Tyr Asn Leu Leu Phe Leu Phe Ser Ile Gly Ile Asp Lys Thr
    530                 535                 540 aaa gca ctg agc ctg ctg cgt gct ctg act gac ttt aaa cgt gcg ttc   1680
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa   1728
Asp Leu Asn Leu Arg Val Lys Asn Met Leu Pro Ser Leu Tyr Arg Glu
                565                 570                 575 gat cct gaa ttc tat gaa aac atg cgt att cag gaa ctg gct cag aat   1776
Asp Pro Glu Phe Tyr Glu Asn Met Arg Ile Gln Glu Leu Ala Gln Asn
            580                 585                 590 atc cac aaa ctg att gtt cac cac aat ctg ccg gat ctg atg tat cgc   1824
Ile His Lys Leu Ile Val His His Asn Leu Pro Asp Leu Met Tyr Arg
        595                 600                 605 gca ttt gaa gtg ctg ccg acg atg gta atg act ccg tat gct gca ttc   1872
Ala Phe Glu Val Leu Pro Thr Met Val Met Thr Pro Tyr Ala Ala Phe
    610                 615                 620
```

```
cag aaa gag ctg cac ggt atg acc gaa gaa gtt tac ctc gac gaa atg      1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt      1968
Val Gly Arg Ile Asn Ala Asn Met Ile Leu Pro Tyr Pro Pro Gly Val
                645                 650                 655 cct ctg gta atg ccg ggt gaa atg atc acc gaa gaa agc cgt ccg gtt      2016
Pro Leu Val Met Pro Gly Glu Met Ile Thr Glu Glu Ser Arg Pro Val
            660                 665                 670 ctg gag ttc ctg cag atg ctg tgt gaa atc ggc gct cac tat ccg ggc      2064
Leu Glu Phe Leu Gln Met Leu Cys Glu Ile Gly Ala His Tyr Pro Gly
        675                 680                 685 ttt gaa acc gat att cac ggt gca tac cgt cag gct gat ggc cgc tat      2112
Phe Glu Thr Asp Ile His Gly Ala Tyr Arg Gln Ala Asp Gly Arg Tyr
    690                 695                 700 acc gtt aag gta ttg aaa gaa gaa agc aaa aaa taa                      2148
Thr Val Lys Val Leu Lys Glu Glu Ser Lys Lys
705                 710                 715

<210> SEQ ID NO 43
<211> LENGTH: 715
<212> TYPE: PRT
<213> ORGANISM: Escherichia coli

<400> SEQUENCE: 43

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
    210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255
```

-continued

```
Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
            275                 280                 285

Val Lys Glu Thr Pro Asn Ala Thr Trp Pro Val His Ala Val Ile Thr
290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
            355                 360                 365

Leu Ala Ala Phe Ser Gln Ala Ser Met Ile His Val Lys Gly Asp Val
        370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415

Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
        435                 440                 445

Trp Phe Phe Asp Val Trp Gln Pro Asp His Ile Asp Thr Thr Glu Cys
    450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
        515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685
```

```
Phe Glu Thr Asp Ile His Gly Ala Tyr Arg Gln Ala Asp Gly Arg Tyr
            690                 695                 700

Thr Val Lys Val Leu Lys Glu Ser Lys Lys
705                 710             715

<210> SEQ ID NO 44
<211> LENGTH: 2142
<212> TYPE: DNA
<213> ORGANISM: Escherichia coli
<220> FEATURE:
<221> NAME/KEY: CDS
<222> LOCATION: (1)..(2142)

<400> SEQUENCE: 44 atg aac atc att gcc att atg gga ccg cat ggc gtc ttt tat aaa gat      48
Met Asn Ile Ile Ala Ile Met Gly Pro His Gly Val Phe Tyr Lys Asp
1               5                   10                  15 gag ccc atc aaa gaa ctg gag tcg gcg ctg gtg gca caa ggc ttt cag      96
Glu Pro Ile Lys Glu Leu Glu Ser Ala Leu Val Ala Gln Gly Phe Gln
                20                  25                  30 att atc tgg cca caa aac agc gtt gat ttg ctg aaa ttt atc gag cat     144
Ile Ile Trp Pro Gln Asn Ser Val Asp Leu Leu Lys Phe Ile Glu His
            35                  40                  45 aac cct cga att tgc ggc gtg att ttt gac tgg gat gag tac agt ctc     192
Asn Pro Arg Ile Cys Gly Val Ile Phe Asp Trp Asp Glu Tyr Ser Leu
        50                  55                  60 gat tta tgt agc gat atc aat cag ctt aat gaa tat ctc ccg ctt tat     240
Asp Leu Cys Ser Asp Ile Asn Gln Leu Asn Glu Tyr Leu Pro Leu Tyr
65                  70                  75                  80 gcc ttc atc aac acc cac tcg acg atg gat gtc agc gtg cag gat atg     288
Ala Phe Ile Asn Thr His Ser Thr Met Asp Val Ser Val Gln Asp Met
                85                  90                  95 cgg atg gcg ctc tgg ttt ttt gaa tat gcg ctg ggg cag gcg gaa gat     336
Arg Met Ala Leu Trp Phe Phe Glu Tyr Ala Leu Gly Gln Ala Glu Asp
                100                 105                 110 atc gcc att cgt atg cgt cag tac acc gac gaa tat ctt gat aac att     384
Ile Ala Ile Arg Met Arg Gln Tyr Thr Asp Glu Tyr Leu Asp Asn Ile
            115                 120                 125 aca ccg ccg ttc acg aaa gcc ttg ttt acc tac gtc aaa gag cgg aag     432
Thr Pro Pro Phe Thr Lys Ala Leu Phe Thr Tyr Val Lys Glu Arg Lys
        130                 135                 140 tac acc ttt tgt acg ccg ggg cat atg ggc ggc acc gca tat caa aaa     480
Tyr Thr Phe Cys Thr Pro Gly His Met Gly Gly Thr Ala Tyr Gln Lys
145                 150                 155                 160 agc ccg gtt ggc tgt ctg ttt tat gat ttt ttc ggc ggg aat act ctt     528
Ser Pro Val Gly Cys Leu Phe Tyr Asp Phe Phe Gly Gly Asn Thr Leu
                165                 170                 175 aag gct gat gtc tct att tcg gtc acc gag ctt ggt tcg ttg ctc gac     576
Lys Ala Asp Val Ser Ile Ser Val Thr Glu Leu Gly Ser Leu Leu Asp
                180                 185                 190 cac acc ggg cca cac ctg gaa gcg gaa gag tac atc gcg cgg act ttt     624
His Thr Gly Pro His Leu Glu Ala Glu Glu Tyr Ile Ala Arg Thr Phe
            195                 200                 205 ggc gcg gaa cag agt tat atc gtt acc aac gga aca tcg acg tcg aac     672
Gly Ala Glu Gln Ser Tyr Ile Val Thr Asn Gly Thr Ser Thr Ser Asn
        210                 215                 220 aaa att gtg ggt atg tac gcc gcg cca tcc ggc agt acg ctg ttg atc     720
Lys Ile Val Gly Met Tyr Ala Ala Pro Ser Gly Ser Thr Leu Leu Ile
225                 230                 235                 240 gac cgc aat tgt cat aaa tcg ctg gcg cat ctg ttg atg atg aac gat     768
Asp Arg Asn Cys His Lys Ser Leu Ala His Leu Leu Met Met Asn Asp
                245                 250                 255
```

```
gta gtg cca gtc tgg ctg aaa ccg acg cgt aat gcg ttg ggg att ctt      816
Val Val Pro Val Trp Leu Lys Pro Thr Arg Asn Ala Leu Gly Ile Leu
        260                 265                 270 ggt ggg atc ccg cgc cgt gaa ttt act cgc gac agc atc gaa gag aaa      864
Gly Gly Ile Pro Arg Arg Glu Phe Thr Arg Asp Ser Ile Glu Glu Lys
            275                 280                 285 gtc gct gct acc acg caa gca caa tgg ccg gtt cat gcg gtg atc acc      912
Val Ala Ala Thr Thr Gln Ala Gln Trp Pro Val His Ala Val Ile Thr
290                 295                 300 aac tcc acc tat gat ggc ttg ctc tac aac acc gac tgg atc aaa cag      960
Asn Ser Thr Tyr Asp Gly Leu Leu Tyr Asn Thr Asp Trp Ile Lys Gln
305                 310                 315                 320 acg ctg gat gtc ccg tcg att cac ttc gat tct gcc tgg gtg ccg tac     1008
Thr Leu Asp Val Pro Ser Ile His Phe Asp Ser Ala Trp Val Pro Tyr
                325                 330                 335 acc cat ttt cat ccg atc tac cag ggt aaa agt ggt atg agc ggc gag     1056
Thr His Phe His Pro Ile Tyr Gln Gly Lys Ser Gly Met Ser Gly Glu
            340                 345                 350 cgt gtt gcg gga aaa gtg atc ttc gaa acg caa tcg acc cac aaa atg     1104
Arg Val Ala Gly Lys Val Ile Phe Glu Thr Gln Ser Thr His Lys Met
        355                 360                 365 ctg gcg gcg tta tcg cag gct tcg ctg atc cac att aaa ggc gag tat     1152
Leu Ala Ala Leu Ser Gln Ala Ser Leu Ile His Ile Lys Gly Glu Tyr
    370                 375                 380 gac gaa gag gcc ttt aac gaa gcc ttt atg atg cat acc acc acc tcg     1200
Asp Glu Glu Ala Phe Asn Glu Ala Phe Met Met His Thr Thr Thr Ser
385                 390                 395                 400 ccc agt tat ccc att gtt gct tcg gtt gag acg gcg gcg gcg atg ctg     1248
Pro Ser Tyr Pro Ile Val Ala Ser Val Glu Thr Ala Ala Ala Met Leu
                405                 410                 415 cgt ggt aat ccg ggc aaa cgg ctg att aac cgt tca gta gaa cga gct     1296
Arg Gly Asn Pro Gly Lys Arg Leu Ile Asn Arg Ser Val Glu Arg Ala
            420                 425                 430 ctg cat ttt cgc aaa gag gtc cag cgg ctg cgg gaa gag tct gac ggt     1344
Leu His Phe Arg Lys Glu Val Gln Arg Leu Arg Glu Glu Ser Asp Gly
        435                 440                 445 tgg ttt ttc gat atc tgg caa ccg ccg cag gtg gat gaa gcc gaa tgc     1392
Trp Phe Phe Asp Ile Trp Gln Pro Pro Gln Val Asp Glu Ala Glu Cys
    450                 455                 460 tgg ccc gtt gcg cct ggc gaa cag tgg cac ggc ttt aac gat gcg gat     1440
Trp Pro Val Ala Pro Gly Glu Gln Trp His Gly Phe Asn Asp Ala Asp
465                 470                 475                 480 gcc gat cat atg ttt ctc gat ccg gtt aaa gtc act att ttg aca ccg     1488
Ala Asp His Met Phe Leu Asp Pro Val Lys Val Thr Ile Leu Thr Pro
                485                 490                 495 ggg atg gac gag cag ggc aat atg agc gag gag ggg atc ccg gcg gcg     1536
Gly Met Asp Glu Gln Gly Asn Met Ser Glu Glu Gly Ile Pro Ala Ala
            500                 505                 510 ctg gta gca aaa ttc ctc gac gaa cgt ggg atc gta gta gag aaa acc     1584
Leu Val Ala Lys Phe Leu Asp Glu Arg Gly Ile Val Val Glu Lys Thr
        515                 520                 525 ggc cct tat aac ctg ctg ttt ctc ttt agt att ggc atc gat aaa acc     1632
Gly Pro Tyr Asn Leu Leu Phe Leu Phe Ser Ile Gly Ile Asp Lys Thr
    530                 535                 540 aaa gca atg gga tta ttg cgt ggg ttg acg gaa ttc aaa cgc tct tac     1680
Lys Ala Met Gly Leu Leu Arg Gly Leu Thr Glu Phe Lys Arg Ser Tyr
545                 550                 555                 560 gat ctc aac ctg cgg atc aaa aat atg cta ccc gat ctc tat gca gaa     1728
Asp Leu Asn Leu Arg Ile Lys Asn Met Leu Pro Asp Leu Tyr Ala Glu
                565                 570                 575
```

```
gat ccc gat ttc tac cgc aat atg cgt att cag gat ctg gca caa ggg    1776
Asp Pro Asp Phe Tyr Arg Asn Met Arg Ile Gln Asp Leu Ala Gln Gly
            580                 585                 590 atc cat aag ctg att cgt aaa cac gat ctt ccc ggt ttg atg ttg cgg    1824
Ile His Lys Leu Ile Arg Lys His Asp Leu Pro Gly Leu Met Leu Arg
        595                 600                 605 gca ttc gat act ttg ccg gag atg atc atg acg cca cat cag gca tgg    1872
Ala Phe Asp Thr Leu Pro Glu Met Ile Met Thr Pro His Gln Ala Trp
    610                 615                 620 caa cga caa att aaa ggc gaa gta gaa acc att gcg ctg gaa caa ctg    1920
Gln Arg Gln Ile Lys Gly Glu Val Glu Thr Ile Ala Leu Glu Gln Leu
625                 630                 635                 640 gtc ggt aga gta tcg gca aat atg atc ctg cct tat cca ccg ggc gta    1968
Val Gly Arg Val Ser Ala Asn Met Ile Leu Pro Tyr Pro Pro Gly Val
                645                 650                 655 ccg ctg ttg atg cct gga gaa atg ctg acc aaa gag agc cgc aca gta    2016
Pro Leu Leu Met Pro Gly Glu Met Leu Thr Lys Glu Ser Arg Thr Val
            660                 665                 670 ctc gat ttt cta ctg atg ctt tgt tcc gtc ggg caa cat tac ccc ggt    2064
Leu Asp Phe Leu Leu Met Leu Cys Ser Val Gly Gln His Tyr Pro Gly
        675                 680                 685 ttt gaa acg gat att cac ggc gcg aaa cag gac gaa gac ggc gtt tac    2112
Phe Glu Thr Asp Ile His Gly Ala Lys Gln Asp Glu Asp Gly Val Tyr
    690                 695                 700 cgc gta cga gtc cta aaa atg gcg gga taa                            2142
Arg Val Arg Val Leu Lys Met Ala Gly
705                 710

<210> SEQ ID NO 45
<211> LENGTH: 713
<212> TYPE: PRT
<213> ORGANISM: Escherichia coli

<400> SEQUENCE: 45

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Asn Thr Leu
                165                 170                 175

Lys Ala Asp Val Ser Ile Ser Val Thr Glu Leu Gly Ser Leu Leu Asp
            180                 185                 190
```

```
His Thr Gly Pro His Leu Glu Ala Glu Glu Tyr Ile Ala Arg Thr Phe
            195                 200                 205
Gly Ala Glu Gln Ser Tyr Ile Val Thr Asn Gly Thr Ser Thr Ser Asn
    210                 215                 220
Lys Ile Val Gly Met Tyr Ala Ala Pro Ser Gly Ser Thr Leu Leu Ile
225                 230                 235                 240
Asp Arg Asn Cys His Lys Ser Leu Ala His Leu Leu Met Met Asn Asp
                245                 250                 255
Val Val Pro Val Trp Leu Lys Pro Thr Arg Asn Ala Leu Gly Ile Leu
            260                 265                 270
Gly Gly Ile Pro Arg Arg Glu Phe Thr Arg Asp Ser Ile Glu Glu Lys
        275                 280                 285
Val Ala Ala Thr Thr Gln Ala Gln Trp Pro Val His Ala Val Ile Thr
    290                 295                 300
Asn Ser Thr Tyr Asp Gly Leu Leu Tyr Asn Thr Asp Trp Ile Lys Gln
305                 310                 315                 320
Thr Leu Asp Val Pro Ser Ile His Phe Asp Ser Ala Trp Val Pro Tyr
                325                 330                 335
Thr His Phe His Pro Ile Tyr Gln Gly Lys Ser Gly Met Ser Gly Glu
            340                 345                 350
Arg Val Ala Gly Lys Val Ile Phe Glu Thr Gln Ser Thr His Lys Met
        355                 360                 365
Leu Ala Ala Leu Ser Gln Ala Ser Leu Ile His Ile Lys Gly Glu Tyr
    370                 375                 380
Asp Glu Glu Ala Phe Asn Glu Ala Phe Met Met His Thr Thr Thr Ser
385                 390                 395                 400
Pro Ser Tyr Pro Ile Val Ala Ser Val Glu Thr Ala Ala Ala Met Leu
                405                 410                 415
Arg Gly Asn Pro Gly Lys Arg Leu Ile Asn Arg Ser Val Glu Arg Ala
            420                 425                 430
Leu His Phe Arg Lys Glu Val Gln Arg Leu Arg Glu Glu Ser Asp Gly
        435                 440                 445
Trp Phe Phe Asp Ile Trp Gln Pro Pro Gln Val Asp Glu Ala Glu Cys
    450                 455                 460
Trp Pro Val Ala Pro Gly Glu Gln Trp His Gly Phe Asn Asp Ala Asp
465                 470                 475                 480
Ala Asp His Met Phe Leu Asp Pro Val Lys Val Thr Ile Leu Thr Pro
                485                 490                 495
Gly Met Asp Glu Gln Gly Asn Met Ser Glu Glu Gly Ile Pro Ala Ala
            500                 505                 510
Leu Val Ala Lys Phe Leu Asp Glu Arg Gly Ile Val Val Glu Lys Thr
        515                 520                 525
Gly Pro Tyr Asn Leu Leu Phe Leu Phe Ser Ile Gly Ile Asp Lys Thr
    530                 535                 540
Lys Ala Met Gly Leu Leu Arg Gly Leu Thr Glu Phe Lys Arg Ser Tyr
545                 550                 555                 560
Asp Leu Asn Leu Arg Ile Lys Asn Met Leu Pro Asp Leu Tyr Ala Glu
                565                 570                 575
Asp Pro Asp Phe Tyr Arg Asn Met Arg Ile Gln Asp Leu Ala Gln Gly
            580                 585                 590
Ile His Lys Leu Ile Arg Lys His Asp Leu Pro Gly Leu Met Leu Arg
        595                 600                 605
Ala Phe Asp Thr Leu Pro Glu Met Ile Met Thr Pro His Gln Ala Trp
    610                 615                 620
```

```
Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
                660                 665                 670

Leu Asp Phe Leu Leu Met Leu Cys Ser Val Gly Gln His Tyr Pro Gly
            675                 680                 685

Phe Glu Thr Asp Ile His Gly Ala Lys Gln Asp Glu Asp Gly Val Tyr
        690                 695                 700

Arg Val Arg Val Leu Lys Met Ala Gly
705                 710

<210> SEQ ID NO 46
<211> LENGTH: 54
<212> TYPE: DNA
<213> ORGANISM: Artificial Sequence
<220> FEATURE:
<223> OTHER INFORMATION: cadA-attL

<400> SEQUENCE: 46
tttgctttct tctttcaata ccttaacggt atagcgtgaa gcctgctttt ttat          54

<210> SEQ ID NO 47
<211> LENGTH: 54
<212> TYPE: DNA
<213> ORGANISM: Artificial Sequence
<220> FEATURE:
<223> OTHER INFORMATION: cadA-attR

<400> SEQUENCE: 47
agatatgact atgaacgtta ttgcaatatt gaatcacgct caagttagta taaa          54

<210> SEQ ID NO 48
<211> LENGTH: 54
<212> TYPE: DNA
<213> ORGANISM: Artificial Sequence
<220> FEATURE:
<223> OTHER INFORMATION: cadL-attL

<400> SEQUENCE: 48
ggaggaacac atgaacatca ttgccattat gggacctgaa gcctgctttt ttat          54

<210> SEQ ID NO 49
<211> LENGTH: 53
<212> TYPE: DNA
<213> ORGANISM: Artificial Sequence
<220> FEATURE:
<223> OTHER INFORMATION: ldcC-attR

<400> SEQUENCE: 49
cgccattttt aggactcgta cgcggtaaac gccgtccgtc aagttagtat aaa           53
```

US 8,354,255 B2

L-AMINO ACID-PRODUCING BACTERIUM AND A METHOD FOR PRODUCING L-AMINO ACIDS

This application claims priority under 35 U.S.C. §119 to Japanese Patent Application No. 2005-279025, filed on Sep. 27, 2005, U.S. Provisional Patent Application No. 60/723,938, filed on Oct. 6, 2005, and Japanese Patent Application No. 2005-360671, filed on Dec. 14, 2005, and is a continuation application under 35 U.S.C. §120 to PCT Patent Application No. PCT/JP2006/319636, filed on Sep. 25, 2006, the contents of which are incorporated by reference in their entireties. The Sequence Listing filed electronically herewith is also hereby incorporated by reference in its entirety (File Name: US-252_Seq_List_Copy_1; File Size: 81 KB; Date Created: Mar. 27, 2008).

BACKGROUND OF THE INVENTION

1. Technical Field

The present invention relates to a method for producing an L-amino acid using a microorganism, and more specifically, to a method for producing an L-amino acid, such as L-lysine, L-threonine, and L-glutamic acid, etc. L-lysine and L-threonine are typically used as animal feed additives, health food ingredients, amino acid infusions, etc., and L-glutamic acid is typically used as a seasoning. Therefore, these are industrially useful L-amino acids.

2. Background Art

L-amino acids are industrially produced employing fermentation methods using microorganisms of the genera Brevibacterium, Corynebacterium, and Escherichia, etc. (EP0857784, 0999267, 1170358, JP11-192088A, WO00/53726, WO96/17930, WO03/04674). Wild-type microorganisms, artificial mutants of said bacterial strains, and microorganisms which have been modified so that the activities of the L-amino acid biosynthesis enzymes are enhanced by recombinant DNA techniques are typically used for L-amino acid production.

Known methods for enhancing the ability of various strains to produce an L-amino acid include modifying the L-amino acid uptake or export. For example, to modify the uptake, the ability to produce L-amino acids is enhanced by deleting or reducing the L-amino acid uptake into the cell. For example, one approach is to delete or lower L-glutamic acid uptake by deleting the gluABCD operon or a part of the operon (EP1038970), etc.

One of the methods for modifying the export of an L-amino acid is to delete or reduce the export of an L-amino acid biosynthetic intermediate, and another method is to strengthen the L-amino acid export. For the former, if the target amino acid is L-glutamic acid, reducing the export of α-ketoglutarate, which is an intermediate in the biosynthesis of L-glutamic acid, by mutating or disrupting the α-ketoglutarate permease gene has been reported (WO01/005959).

To delete or reduce the export of an L-amino acid biosynthetic intermediate, methods for overexpressing genes responsible for L-amino acid export have been reported, for example, producing L-lysine (WO97/23597) or L-arginine using a bacterial strain of a microorganism of the genus Corynebacterium with enhanced expression of the L-lysine or L-arginine export gene (LysE) (Journal of Molecular Microbiology Biotechnology (J Mol Microbiol Biotechnol) 1999 November; 1(2):327-36). Furthermore, increasing the expression of the rhtA, B, and C genes (U.S. Pat. No. 6,303,348), or the yfiK, yahN genes, etc. has been reported as a method for producing L-amino acids in an Escherichia bacteria (EP 1013765).

Aside from modifying the L-amino acid biosynthesis pathway and modifying the uptake and export of the L-amino acid as described above, modifying the ability of the bacteria to take up sugar is another example of a method for improving L-amino acid production. For example, the phosphoenolpyruvate:carbohydrate phosphotransferase system (hereinafter, also referred to as PTS: phosphotransferase) is widely known as a transporter which functions to uptake sugar. Furthermore, PTS is classified as a substrate-independent common system EI (encoded by ptsI), HPr (encoded by ptsH), or substrate-specific component EII. Glucose-specific EII is encoded by ptsG and crr, with the crr gene being a part of an operon with ptsH and ptsI. One known method for producing an L-amino acid uses the genus Escherichia in which the ptsG gene has been enhanced (WO03/04670), and another method uses the genus Escherichia in which the ptsH, ptsI, and crr genes have been enhanced (WO03/04674).

Aside from the glucose PTS mentioned above, the bglF gene is known to encode β-glucoside specific phosphotransferase (PTS) (Journal of Bacteriology, 1999, Vol. 18, No. 2, p 462-468, Biochemistry, 1998, Vol. 37, p 17040-17047, Biochemistry, 1998, Vol. 37, p 8714-8723), but the use of a gene encoding PTS other than glucose PTS for the production of an L-amino acid has not been reported.

SUMMARY OF THE INVENTION

An aspect of the present invention is to provide a bacterial strain which is capable of efficiently producing an L-amino acid and to also provide a method for producing an L-amino acid using said bacterial strain.

In order to resolve the above-mentioned problem, it has been discovered that an L-amino acid can be effectively produced using a microorganism belonging to the family Enterobacteriaceae which has been modified to increase β-glucoside PTS activity. That is, the present invention is as follows:

It is an aspect of the present invention to provide a method for producing an L-amino acid comprising culturing in a medium a microorganism of the Enterobacteriaceae family which has an ability to produce an L-amino acid and which has been modified to enhance β-glucoside PTS activity as compared to a non-modified microorganism, and collecting the L-amino acid from the medium or cells.

It is an aspect of the present invention to provide the method described above, wherein said β-glucoside PTS activity is enhanced by increasing expression of the bglF gene by a method selected from the group consisting of A) increasing the copy number of the gene, B) modifying an expression regulatory sequence of the gene, and C) combinations thereof.

It is an aspect of the present invention to provide the method described above, wherein said bglF gene is selected from the group consisting of:

(a) a DNA comprising the nucleotide sequence of SEQ ID No. 5, (b) a DNA encoding a protein having β-glucoside PTS activity which hybridizes with: i) a sequence complementary to nucleotide sequence of SEQ ID No. 5, or ii) a probe prepared from said nucleotide sequence under stringent conditions.

It is an aspect of the present invention to provide the method as described above, wherein the bglF gene encodes a protein selected from the group consisting of: A) a protein comprising the amino acid sequence of SEQ ID NO: 6, and B)

a protein comprising the amino acid sequence of SEQ ID NO: 6, but which includes one or more amino acid substitutions, deletions, additions, or inversions and has β-glucoside PTS activity.

It is an aspect of the present invention to provide the method described above, wherein the microorganism is a bacterium of the genus *Escherichia* or genus *Pantoea*.

It is an aspect of the present invention to provide a method described above, wherein said L-amino acid is selected from a group consisting of L-lysine, L-threonine, L-glutamic acid, and combinations thereof.

DESCRIPTION OF THE PREFERRED EMBODIMENTS

Figure 1:
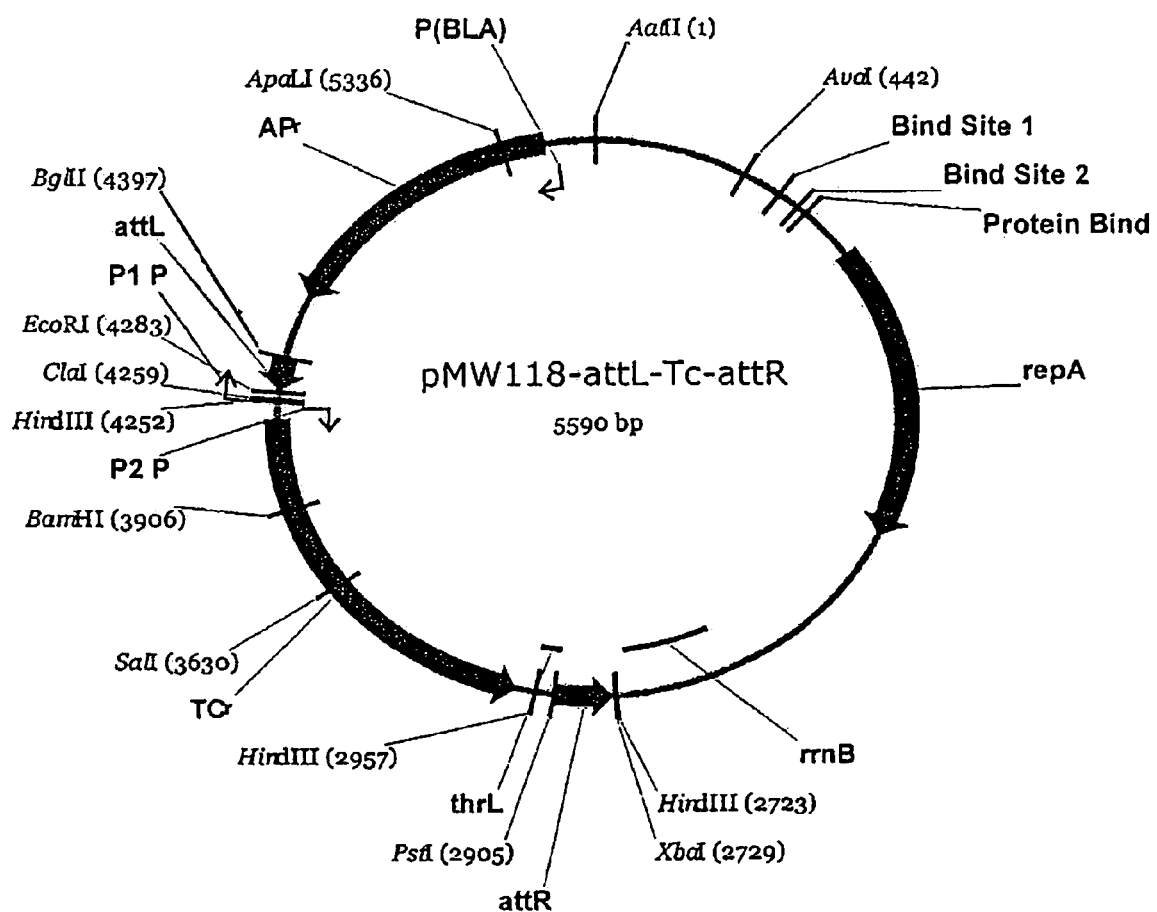
FIG. 1 shows the construction of the plasmid pMW118-attL-Tc-attR.
Figure 2:
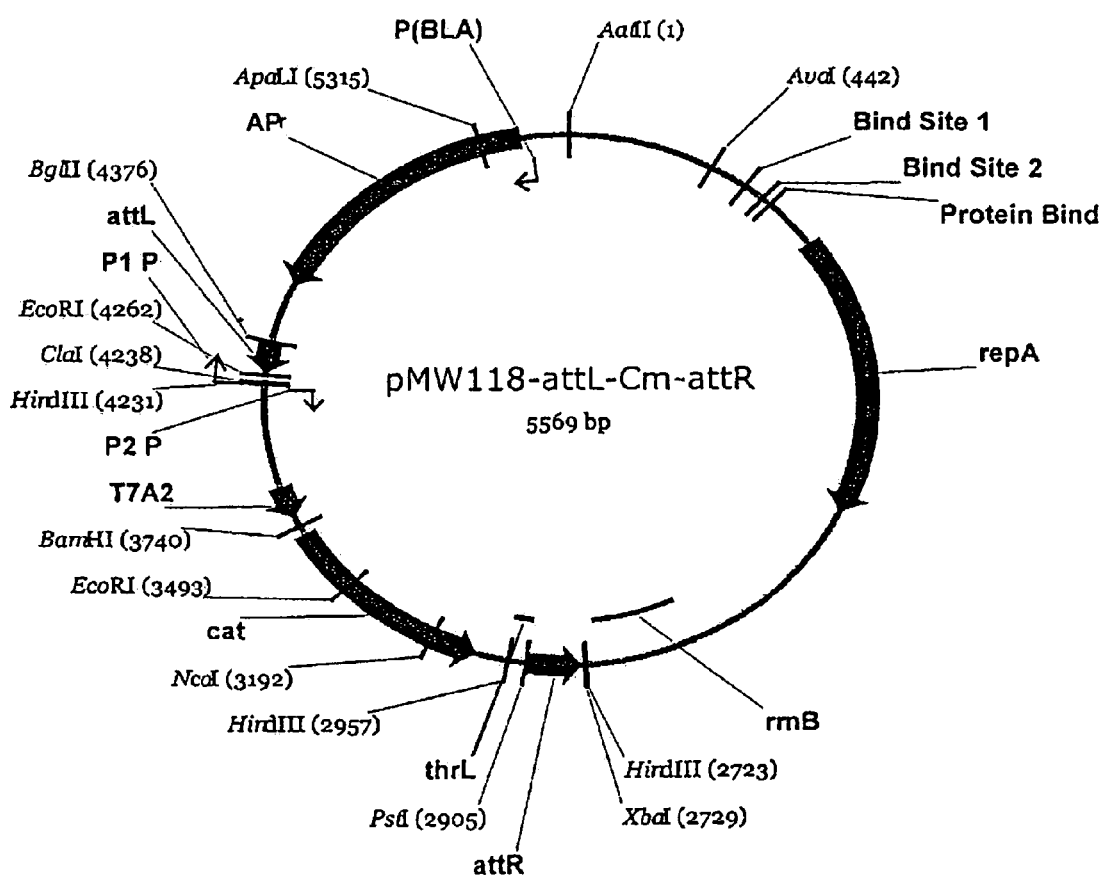
FIG. 2 shows the construction of the plasmid pMW118-attL-Cm-attR.
Figure 3:
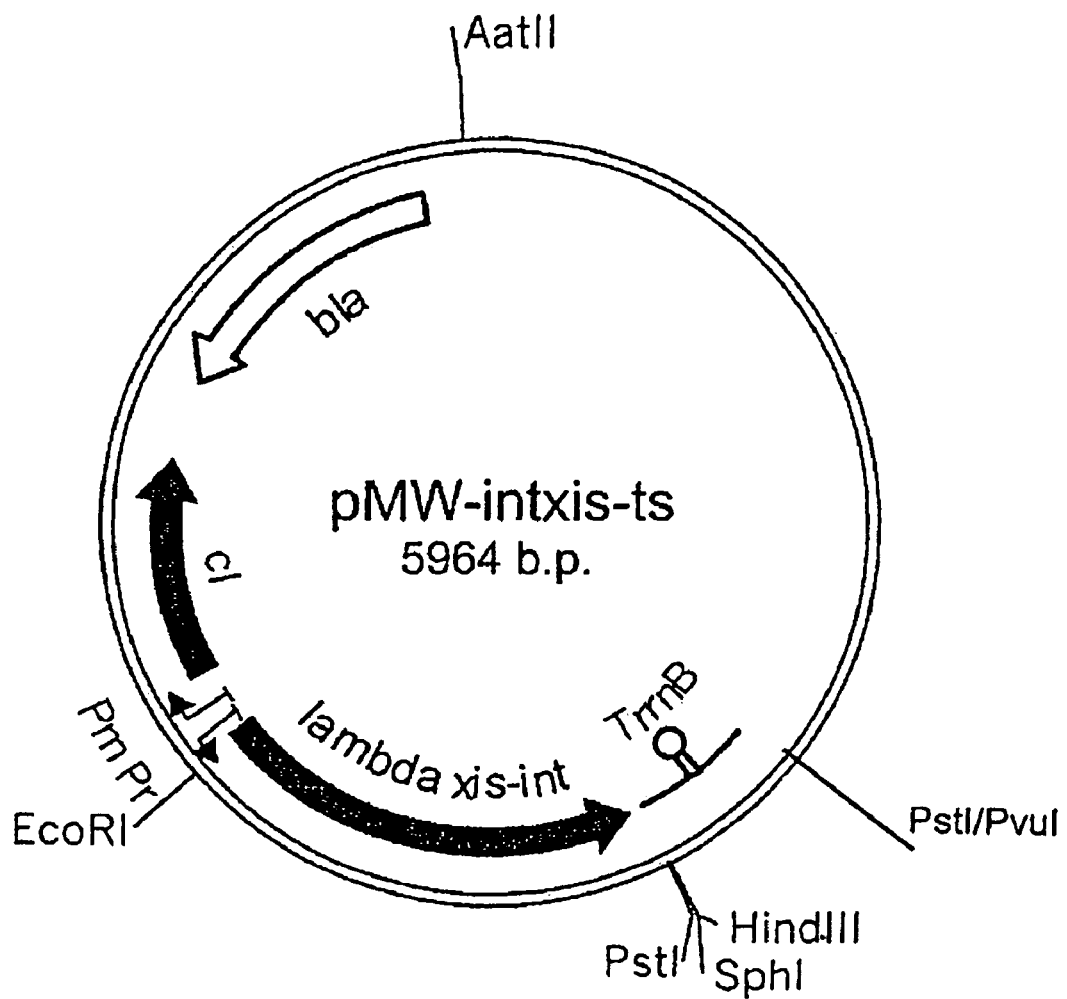
FIG. 3 shows the construction of the plasmid pMW-intxis-ts.

Hereinafter, the present invention will be explained in detail.

<1> The Microorganism of the Present Invention

The microorganism of the present invention is of the Enterobacteriaceae family and has an ability to produce an L-amino acid. This microorganism also has been modified to enhance the β-glucoside PTS activity. The phrase "an ability to produce an L-amino acid" means the ability to produce and cause accumulation of an L-amino acid in a medium or in the cells of the microorganism when the microorganism of the present invention is cultured in the medium. The microorganism of the present invention may have the ability to produce multiple L-amino acids. The microorganism may inherently possesses the ability to produce an L-amino acid, or may be modified by mutagenesis or recombinant DNA techniques to impart the ability to produce an L-amino acid, such as those described below.

The type of L-amino acid is not particularly limited. Examples of the L-amino acid include the basic L-amino acids such as L-lysine, L-ornithine, L-arginine, L-histidine, and L-citrulline; the aliphatic L-amino acids such as L-isoleucine, L-alanine, L-valine, L-leucine, and L-glycine; the hydroxyl L-amino acids such as L-threonine and L-serine; the cyclic L-amino acids such as L-proline; the aromatic L-amino acids such as L-phenylalanine, L-tyrosine, and L-tryptophan; the sulfur-containing L-amino acids such as L-cysteine, L-cystine, and L-methionine; and the acidic L-amino acid such as L-glutamic acid, L-aspartic acid; the amides of acidic L-amino acid such as L-glutamine, L-asparagine, etc. The microorganism of the present invention may have the ability to produce two or more amino acids.

<1-1> Imparting L-Amino Acid-Producing Ability

The following examples include a description of the method for imparting L-amino acid-producing ability, along with examples of microorganisms imparted with L-amino acid-producing ability which can be used in the present invention. The microorganisms of the present invention are not limited to these, but can be any as long as they have L-amino acid-producing ability.

There is no particular limitation on the microorganism used in the present invention, as long as it belongs to the family Enterobacteriaceae, such as the genera *Escherichia*, *Enterobacter*, *Pantoea*, *Klebsiella*, *Serratia*, *Erwinia*, *Salmonella*, *Morganella*, etc., and it has an L-amino acid-producing ability. Specifically, any microorganism belonging to the family Enterobacteriaceae as classified in the NCBI (National Center for Biotechnology Information) database may be used.

It is particularly desirable to use bacteria which belong to the genera *Escherichia*, *Enterobacter*, or *Pantoea* when modifying parent bacterial species.

The parent bacterial strain of the genus *Escherichia* used to obtain the bacteria of the present invention is not particularly limited, but strains listed by Neidhardt et al., may be used (Neidhardt, F. C. et al., *Escherichia coli* and *Salmonella Typhimurium*, American Society for Microbiology, Washington, D.C., 1029 table 1). One example is *Escherichia coli*. Specific examples of *Escherichia coli* are *Escherichia coli* W3110 (ATCC 27325), *Escherichia coli* MG1655 (ATCC 47076), etc., which are prototypes derived from wild-type strains of K12.

These are available, for example, from the American Type Culture Collection (address: P.O. Box 1549 Manassas, Va. 20108, USA). They are available via use of the accession number given to each bacterial strain (see http:/www.atcc.org). The accession numbers correspond to each bacterial strain, and are listed in the American Type Culture Collection's catalogue.

Examples of bacteria of the genus *Enterobacter* include *Enterobacter agglomerans* and *Enterobacter aerogenes*. An example of a bacterium of the genus *Pantoea* is *Pantoea ananatis*. In recent years, based on 16S rRNA nucleotide sequence analysis, *Enterobacter agglomerans* has on occasion been reclassified as *Pantoea agglomerans*, *Pantoea ananatis*, and *Pantoea stewartii*. For the present invention, any bacterium classified in the family Enterobacteriaceae, whether *Enterobacter* or *Pantoea*, may be employed. The strains *Pantoea ananatis* AJ13355 (FERM BP-6614), AJ13356 (FERM BP-6615), AJ13601 (FERM BP-7207), or any derivative thereof may be employed to breed *Pantoea ananatis* by genetic engineering methods. When isolated, these strains were identified and deposited as *Enterobacter agglomerans*. As stated above, by analysis using the 16S rRNA nucleotide sequence, these bacteria have been reclassified as *Pantoea ananatis*. For the present invention, any bacterium belonging to the genus *Enterobacter* or *Pantoea* may be used as long as the bacterium is classified in the family Enterobacteriaceae.

The following is a description of methods for imparting an L-amino acid-producing ability to a microorganism which belongs to the Enterobacteriaceae family.

To impart the ability to produce an L-amino acid, an auxotrophic mutant, an analog-resistant strain, or a metabolic regulation mutant can be obtained, or a recombinant strain having enhanced expression of an L-amino acid biosynthesis enzyme can be created. Methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can also be utilized. Here, in the breeding of an L-amino acid-producing bacteria, one or more properties, such as auxotrophic mutation, analog resistance, or metabolic regulation mutation may be imparted. Enhancing the expression of one or more L-amino acid biosynthesis enzymes may also be employed. Furthermore, imparting properties such as auxotrophic mutation, analog resistance, or metabolic regulation mutation may be performed in combination with enhancing the activity of biosynthesis enzymes.

An auxotrophic mutant strain, L-amino acid analog-resistant strain, or metabolic regulation mutant strain with the ability to produce an L-amino acid can be obtained by subjecting a parent or wild-type strain to a conventional mutation treatment, such as treating with X-rays or UV radiation, or treating with a mutagenic agent such as N-methyl-N'-nitro-N-nitrosoguanidine, etc., then selecting those which exhibit an autotrophic mutation, analog resistance, or metabolic regulation mutation and which also have the ability to produce an L-amino acid.

Examples of an L-lysine analog-resistant strain or metabolic regulation mutant include, but are not limited to, the *Escherichia coli* AJ11442 strain (FERM BP-1543, NRRL B-12185, JP56-18596A, and U.S. Pat. No. 4,346,170), and the *Escherichia coli* VL611 strain (EP1016710A), etc. The *Escherichia coli* WC196 strain (WO96/17930) also produces L-lysine. The WC196 strain was bred by imparting AEC (S-(2-aminoethyl)-cysteine) resistance to the W3110 strain derived from *Escherichia coli* K-12. This strain was named *Escherichia coli* AJ13069, and was deposited on Dec. 6, 1994 with the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14690 and converted to an international deposit under the Budapest Treaty on Sep. 29, 1995, and given Accession No. FERM BP-5252.

L-lysine-producing bacteria can also be constructed by increasing the L-lysine biosynthetic enzyme activity. Examples of genes encoding L-lysine biosynthesis enzymes are the dihydrodipicolinate synthase gene (dapA) (EP 0733710B), aspartokinase gene (lysC) (EP 0733710, U.S. Pat. No. 5,932,453), dihydrodipicolinate reductase gene (dapB), diaminopimelate decarbonylase gene (lysA), diaminopimelate dehydrogenase gene (ddh) (WO96/40934), the phosphoenolpyruvate carboxylase gene (ppc) (JP60-87788A), the aspartate aminotransferase gene (aspC) (JP6-102028A), the diaminopimelate epimerase gene (dapF) (WO00/56858), the aspartate-semialdehyde dehydrogenase gene (asd) (WO00/61723), and other genes of diaminopimelate pathway enzymes; as well as the homoaconitate hydratase gene (JP2000-157276) and other genes of aminoadipate pathway enzymes. The abbreviations for these genes are given in the parentheses following each name.

Furthermore, it is known that the activities of wild-type dihydrodipicolinate synthase (DDPS) and aspartokinase (AK) are inhibited by feedback by L-lysine; therefore, when dapA and lysC are used, it is preferable to use genes encoding mutant dihydrodipicolinate synthase and aspartokinase, respectively, that are resistant to the feedback inhibition by L-lysine (EP 0733710, U.S. Pat. No. 5,932,453).

Examples of the DNA encoding mutant dihydrodipicolinate synthase that is resistant to feedback inhibition by L-lysine include a DNA encoding DDPS having an amino acid sequence wherein the 118th histidine residue is substituted with tyrosine. (U.S. Pat. Nos. 5,661,012 and 6,040,160). Furthermore, examples of the DNA encoding a mutant AK that is resistant to feedback inhibition by L-lysine include a DNA encoding AK having the amino acid sequence wherein the 352-threonine residue is substituted with isoleucine. (U.S. Pat. Nos. 5,661,012 and 6,040,160). These mutant DNAs can be obtained by site-directed mutagenesis using PCR, or the like.

The following is an example of imparting an L-lysine-producing ability by introducing a gene encoding an L-lysine biosynthesis enzyme into the host. That is, recombinant DNA is prepared by ligating the gene fragment that encodes the L-lysine biosynthesis gene with a vector that functions in the host microorganism used in the production of L-lysine, preferably a multi-copy type vector, and this is used to transform the host. By the transformation, the copy number of the gene encoding the L-lysine biosynthesis enzyme in the host cell increases, enhancing the expression and consequently increasing the enzymatic activity.

The genes encoding the L-lysine biosynthesis enzymes are not particularly limited, as long as they can be expressed in the host microorganism. Examples include genes derived from *Escherichia coli*, and genes derived from coryneform bacteria. Because the total genome sequences of *Escherichia coli* and *Corynebacterium glutamicum* have been determined, it is possible to synthesize primers based on the nucleotide sequence of these genes and obtain these genes using the PCR method in which the chromosomal DNA of a microorganism, such as *Escherichia coli* K12, etc., is used as the template.

In order to clone these genes, plasmids that autonomously replicate in the Enterobacteriaceae can be used. Examples include pBR322, pTWV228 (Takara Bio Inc.), pMW119 (Nippon Gene Co., Ltd.), pUC19, pSTV29 (Takara Bio Inc.), RSF110 (Gene vol. 75 (2), pp. 271-288, 1989), etc. In addition, a vector of phage DNA may also be used.

To ligate the target gene to the above-mentioned vector, the vector is digested with a restriction enzyme matched to the end of the DNA fragment containing the target gene. The ligation is usually conducted with a ligase such as T4 DNA ligase. Target genes may be present on separate vectors, respectively, or present on the same vector. Typical methods known to those skilled in the art can be employed for digesting and ligating the DNA, as well as for preparing chromosomal DNA, performing PCR, preparing plasmid DNA, transformation, determining the oligonucleotides for use as primers, etc. These methods are described in Sambrook, J., and Russell, D. W. Molecular Cloning A Laboratory Manual/Third Edition. New York: Cold Spring Harbor Laboratory Press (2001), etc. Any method which achieves adequate transformation efficiency may be employed to introduce recombinant DNA that has been prepared as described above into the microorganism. An example includes electroporation (Canadian Journal of Microbiology, 43, 197 (1997)). An example of a plasmid prepared using electroporation is pCABD2, which contains the dapA, dapB, and LysC genes (WO 01/53459).

Enhancing the expression of genes encoding L-lysine biosynthesis enzymes can also be achieved by introducing multiple copies of the target gene into the chromosomal DNA of a microorganism. Multiple copies of the target gene can be introduced into the chromosomal DNA of the microorganism by using a sequence in which multiple copies are present on the chromosomal DNA as a target in homologous recombination. Such site-specific introduction of mutations based on gene substitution using homologous recombination has been described. Methods employing linear DNA or a plasmid containing a temperature-sensitive replication origin have been described (U.S. Pat. Nos. 6,303,383 and 5,616,480). Repetitive DNA and inverted repeats present on the ends of transposable elements can be employed as sequences in which multiple copies are present on chromosomal DNA. An L-lysine biosynthesis gene may be ligated in tandem with a gene which is inherently present on the chromosome, or it may be introduced into a non-essential region on the chromosome or a region of the gene in which the L-lysine yield will be improved if deleted.

Furthermore, as disclosed in U.S. Pat. No. 5,595,889, the target gene may also be located on a transposon, which is then transferred to introduce multiple copies into the chromosomal DNA. With either method, the number of copies of the target gene in the transformant increases, so that the enzymatic activity of the L-lysine biosynthesis increases.

In addition to the above-described genetic amplification, an increase in the L-lysine biosynthesis enzyme activity can be achieved by replacing an expression regulatory sequence of the target gene, such as a promoter etc., with a stronger one (see JP1-215280A). For example, the lac promoter, trp promoter, trc promoter, tac promoter, lambda phage PR promoter, PL promoter, and tet promoter are all known as strong promoters. Substitution with these promoters increases expression of the target gene, thus enhancing enzymatic activity. Examples of strong promoters and methods for evaluating the strength of promoters are described in an article by Goldstein et al. (Prokaryotic promoters in biotechnology. Biotechnol. Annu. Rev., 1995, 1, 105-128), etc.

Increasing L-lysine biosynthesis enzyme activity can also be achieved by modifying an element involved in the regulation of the target gene expression, for example, the operator or repressor (Hamilton et al.; J. Bacteriol. 1989 September; 171 (9):4617-22). As disclosed in WO 00/18935, a substitution of several bases may be introduced into the −35, −10 region of the promoter of a target gene to modify and strengthen it. Furthermore, substituting several nucleotides into the spacer region between the ribosome binding site (RBS) and the start codon, particularly into the sequence immediately upstream of the start codon, is known to have a strong effect on the mRNA translation efficiency. The expression regulatory regions of the target gene's promoter, etc., can be determined by promoter probe vectors and gene analysis software such as GENETYX, etc. Substitution of expression regulatory sequences can be conducted, for example, in the same manner as in the above-described gene substitution employing temperature-sensitive plasmids. The Red-driven integration method (WO2005/010175) may also used.

Furthermore, in the L-lysine-producing bacteria of the present invention, the activity of an enzyme catalyzing production of a compound other than an L-lysine which branches off from its biosynthesis pathway, or the activity of an enzyme which has a negative effect on the production of L-lysine may be reduced or deleted. These enzymes include homoserine dehydrogenase (thrA), lysine decarboxylase (cadA, lysC), and malic enzyme (sfcA, b2463). The strains with reduced or deficient enzymatic activity are described in WO 95/23864, WO96/17930, WO2005/010175, etc.

To reduce or delete said enzyme activity in a cell, mutagenesis may be performed on the gene which encodes the above-mentioned enzymes, using typical and known methods. This can be achieved, for example, by deleting the gene that encodes the enzyme on the chromosome using genetic recombination, or by modifying the expression regulatory sequence of a promoter or a Shine-Delgarno (SD) sequence, etc. This can also be achieved by introducing an amino acid substitution (missense mutation) or stop codon (nonsense mutation) in the region encoding the enzyme on the chromosome, by introducing a frameshift mutation to add or delete 1-2 bases, or by deleting a part of the gene or the entire region (Journal of Biological Chemistry 272:8611-8617 (1997); Journal of Antimicrobial Chemotherapy 200 46, 793-796; Biotechnol Prog 1999, 15, 58-64; J. Biological Chemistry vol 272 NO. 13 pp 8611-8617). Also, the enzyme activity can be reduced or deleted by constructing a gene that encodes the mutant enzyme in which the encoded region has been deleted and then substituting the wild-type gene on the chromosome with this, by homologous recombination, etc., or introducing a transposon or IS element into said gene.

The following methods may be used to introduce a mutation which reduces or deletes the above-mentioned enzyme activity by genetic recombination. An isolated DNA containing the target gene is mutated so that the resulting mutant gene does not produce an enzyme that functions normally. Then, transforming this into a microorganism which belongs to the family Enterobacteriaceae using the DNA containing the gene, and generating the recombination of the mutant-type gene with a gene on the chromosome. For gene substitution using this kind of homologous recombination, there are methods which employ linear DNA, such as the method called "Red-driven integration" (Proc. Natl. Acad. Sci. USA, 2000, vol. 97, No. 12, pp. 6640-6645), or by combining the Red-driven integration method and the λ phage excisive system (J. Bacteriol. 2002 September; 184 (18): 5200-3, Interactions between integrase and excisionase in the phage lambda excisive nucleoprotein complex. Cho E H, Gumport R I, Gardner J F) (see WO2005/010175), etc.; and there are methods which employ a plasmid containing a temperature-sensitive replication origin (Proc. Natl. Acad. Sci. USA, 2000, vol. 97, No. 12, pp. 6640-6645, U.S. Pat. Nos. 6,303,383, or 5,616,480). Such site-specific introduction of mutations via gene substitution using homologous recombination as described above may also be performed using a plasmid which does not have replication ability in the host.

The above-mentioned method for increasing the enzyme activity involving L-lysine biosynthesis and the method for lowering the enzyme activity may likewise be used in breeding other L-amino acid-producing bacteria. The following is a description of methods for breeding other L-amino acid bacteria.

As the L-glutamic acid-producing bacteria used in the present invention, there is, for example, a microorganism which belongs to the family Enterobacteriaceae which has been modified to increase the expression of a gene encoding an enzyme that is involved in L-glutamic acid biosynthesis. The enzymes involved in L-glutamic acid biosynthesis include glutamate dehydrogenase (gdh), glutamine synthetase (gltAB), glutamate synthase (glnA), isocitrate dehydrogenase (icd), aconitate hydratase (acn), citrate synthase (gltA), phosphoenolpyruvate carboxylase (ppc), pyruvate carboxylase (pycA), pyruvate dehydrogenase (pdhA), pyruvate kinase (pykA), phosphoenolpyruvate synthase (pps), enolase (eno), phosphoglucomutase (pgm), phosphoglycerate kinase (pgk), glyceraldehyde-3-phosphate dehydrogenase (gpd), triose phosphate isomerase (tpi), fructose-bisphosphate aldolase (fba), phosphofructokinase (pfk), glucosephosphate isomerase (gpi), etc. Of these enzymes, citrate synthase, phosphoenolpyruvate carboxylase, glutamate dehydrogenase, and combinations thereof are preferable, and the use of all three is more preferable.

Examples of microorganisms belonging to the family Enterobacteriaceae which have been modified to enhance the expression of the citrate synthase gene, phosphoenolpyruvate carboxylase gene, and/or glutamate dehydrogenase gene using the methods described above are described in U.S. Pat. Nos. 6,197,559 & 6,331,419, EP0999282, and WO2006/051660.

Furthermore, microorganisms belonging to the family Enterobacteriaceae which have been modified to increase the activity of either 6-phosphogluconate dehydratase or 2-keto-3-deoxy-6-phosphogluconate aldolase, or both, may also be used. (EP1352966B)

The microorganisms of the family Enterobacteriaceae having the ability to produce an L-glutamic acid which may be used include a bacterium in which the activity of an enzyme that catalyzes production of a compound other than L-glutamic acid, but which branches off from the biosynthesis pathway of L-glutamic acid, has been reduced or lowered. Examples of such enzymes include 2-oxoglutarate dehydrogenase (sucA), isocitrate lyase (aceA), acetohydroxy acid synthase (ilvG), acetolactate synthase (ilvN), formate acetyltransferase (pflB), lactate dehydrogenase (ldh), glutamate decarboxylase (gadA), and 1-pyrroline dehydrogenase (putA), etc. Of these, it is especially preferable to reduce or delete the activity of 2-oxoglutarate dehydrogenase.

Methods for deleting or reducing the activity of 2-oxoglutarate dehydrogenase in a microorganism belonging to the family Enterobacteriaceae are described in U.S. Pat. Nos. 5,573,945, 6,197,559, and 6,331,419. Examples of microorganisms belonging to the family Enterobacteriaceae wherein the activity of 2-oxoglutarate dehydrogenase has been deleted or reduced include the following:

*Pantoea ananatis* AJ13601 (FERM BP-7207)
*Klebsiella planticola* AJ13410 strain (FERM BP-6617)
*Escherichia coli* AJ12949 (FERM BP-4881), and others.

The AJ12949 strain has reduced α-ketoglutarate dehydrogenase activity, and was deposited on Dec. 28, 1993 with the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14039 and converted to an international deposit under the Budapest Treaty on Nov. 11, 1994, and given Accession No. FERM BP-4881.

The L-tryptophan-producing bacteria preferably used in the present invention are bacteria in which the activity of one or more of the following enzymes, i.e., anthranilate synthase (trpE), phosphoglycerate dehydrogenase (serA), or tryptophan synthase (trpAB) has been enhanced. Since anthranilate synthase and phosphoglycerate dehydrogenase both are subject to feedback inhibition by L-tryptophan and L-serine, the activities of these enzymes can be increased by retaining the desensitizing mutant enzyme (U.S. Pat. Nos. 5,618,716, 6,180,373). For instance, it is possible to obtain bacteria which have a desensitizing enzyme by mutating the anthranilate synthase gene (trpE) and/or the phosphoglycerate dehydrogenase gene (serA) to prevent feedback inhibition, then introducing the mutant gene into a microorganism belonging to the family Enterobacteriaceae. A specific example of this kind of bacteria is *Escherichia coli* SV164 which retains desensitized anthranilate synthase and which has been transformed with plasmid pGH5 having a mutated serA that encodes desensitized phosphoglycerate dehydrogenase (WO94/08301).

Bacteria transformed with recombinant DNA containing a tryptophan operon are also preferable L-tryptophan-producing bacteria. A specific example is *Escherichia coli* transformed with a tryptophan operon containing a gene encoding desensitized anthranilate synthase (trpAB) (Japanese Patent Application Publication No. JP57-71397, Japanese Patent Application Publication No. JP 62-244382, U.S. Pat. No. 4,371,614). Furthermore, in the tryptophan operon, it is possible to enhance the ability to produce L-tryptophan by increasing the expression of the gene (trpBA) encoding tryptophan synthase. Tryptophan synthase contains α and β subunits that are encoded by trpA and trpB, respectively (WO2005/103275).

Examples of L-tryptophan-producing bacteria are *Escherichia coli* AGX17 (pGX44) [NRRL B-12263], which requires L-phenylalanine and L-tyrosine for growth, and AGX6 (pGX50) aroP [NRRL B-12264], which retains plasmid pGX50 containing a tryptophan operon (see U.S. Pat. No. 4,371,614).

A strain with a deficient tryptophan operon repressor (trpR), and a strain with a mutant trpT are also desirable L-tryptophan-producing bacteria. (U.S. Pat. No. 4,371,614 WO2005/056776).

Another preferable L-tryptophan-producing bacterium is the bacterium in which malate synthase (aceB), isocitrate lyase (aceA), and the isocitrate dehydrogenase/phosphatase (icl) operon (ace operon) are structurally expressed, or the expression of said operon has been enhanced (WO2005/103275).

L-tryptophan, L-phenylalanine, and L-tyrosine are all aromatic amino acids and share a biosynthesis system. Examples of genes encoding biosynthesis enzymes of aromatic amino acids include deoxyarabino-heptulosonate phosphate synthase (aroG), 3-dehydroquinate synthase (aroB), shikimate dehydratase, shikimate kinase (aroL), 5-enolpyruvylshikimate[-]3-phosphate synthase (aroA), and chorismate synthase (aroC) (European Patent Application Publication No. 763127). Therefore, by placing multiple copies of the genes encoding these enzymes onto a plasmid or genome, the aromatic amino acid-producing ability can be improved. It is known that these genes are controlled by a tyrosine repressor (tyrR), so the biosynthesis enzyme activity of an aromatic amino acid may also be increased by deleting the tyrR gene (EP763127).

The L-threonine-producing bacteria are preferably microorganisms belonging to the family Enterobacteriaceae wherein the L-threonine biosynthesis enzymes have been enhanced. Examples of genes encoding L-threonine biosynthesis enzymes include the aspartokinase III gene (lysC), the aspartate-semialdehyde dehydrogenase gene (asd), the aspartokinase I gene encoding the thr operon (thrA), the homoserine kinase gene (thrB), and the threonine synthase gene (thrC). The abbreviations for these genes are given in parentheses following their names. One or more of these genes may be introduced. The L-threonine biosynthesis gene may be introduced into a bacterium of the genus *Escherichia* wherein threonine degradation has been suppressed. Examples of bacteria of the genus *Escherichia* wherein threonine degradation has been suppressed include the TDH6 strain wherein the threonine dehydrogenase activity has been deleted (Japanese Patent Application Publication No. 2001-346578), and so forth.

Activities of some of the L-threonine biosynthesis enzymes are suppressed by the L-threonine that is produced. Therefore, in order to construct an L-threonine-producing bacterium, it is preferable to modify the L-threonine biosynthesis enzyme so that the enzyme is not subject to feedback inhibition by L-threonine. The above-mentioned thrA, thrB, and thrC genes make up the threonine operon, which is in the form of an attenuator structure. The expression of the threonine operon is subject to inhibition by isoleucine and threonine present in the culture, and the expression is attenuated. This modification of the threonine operon can be achieved by removing the leader sequence in the attenuation region or the attenuator. (WO 02/26993; Biotechnology Letters Vol. 24, No. 21, November 2002; WO2005/049808).

A native promoter is located on the threonine operon, and may be substituted with a non-native promoter (WO 98/04715). Alternatively, a threonine operon may be constructed so that the expression of the gene involved in threonine biosynthesis is controlled by a lambda phage repressor and promoter. (EP0593792). Also, to prevent feedback inhibition by L-threonine, modification of the bacteria of the genus *Escherichia* can also be obtained by selecting an α-amino-β-hydroxyvaleric acid (AHV) resistant bacterial strain (JP45026708B).

It is preferred that the copy number of the threonine operon which is modified to prevent feedback inhibition by L-threonine is increased in the host or is ligated to a strong promoter. In addition to amplifying the copy number of the gene using a plasmid, the copy number of the gene can be increased by introducing the threonine operon onto the chromosome using a transposon, Mu-phage, etc.

For the aspartokinase III gene (lysC), it is desirable to use a gene modified to prevent feedback inhibition by L-lysine. A lysC gene which has been modified to prevent feedback inhibition can be obtained using the method described in the U.S. Pat. No. 5,932,453.

Aside from the L-threonine biosynthesis enzyme, it is desirable to strengthen genes involved in the glycolytic system, TCA cycle, and respiratory chain, a gene which controls gene expression, and a gene which induces uptake of sugar. Examples of these genes which are effective in L-threonine production include the transhydrogenase gene (pntAB) (EP733712), phosphoenolpyruvate carboxylase gene (ppc) (WO 95/06114), the phosphoenolpyruvate synthase gene (pps) (EP 877090), and the pyruvate carboxylase gene in the coryneform bacteria or *Bacillus* bacteria (WO99/18228, EP1092776).

It is also preferable to enhance the expression of a gene that imparts resistance to L-threonine and a gene that imparts resistance to L-homoserine, or to impart both L-threonine resistance and L-homoserine resistance to the host. Examples of such genes are the rhtA gene (Res Microbiol. 2003 March; 154 (2): 123-35), the rhtB gene (EP0994190), the rhtC gene (EP1013765), the yfiK gene, and the yeaS gene (EP1016710). To impart L-threonine resistance to a host, refer to European Patent Application Publication No. 0994190 and WO 90/04636.

Another example of an L-threonine-producing bacterium is the *Escherichia coli* VKPM B-3996 strain (U.S. Pat. No. 5,175,107). This VKPM B-3996 strain was deposited on Nov. 19, 1987, under Accession No. VKPM B-3996, at the Russian National Collection of Industrial Microorganisms (VKPM), GNII Genetika. In addition, the VKPM B-3996 strain retains plasmid pVIC40 (WO90/04636) obtained by inserting a threonine biosynthesis gene (threonine operon: thrABC) into a wide-host vector plasmid pAY32 including a streptomycin-resistant marker (Chistorerdov, A. Y., Tsygankov, Y. D., Plasmid, 1986, 16, 161-167). In this pVIC40, the feedback inhibition by the L-threonine of the aspartokinase I-homoserine dehydrogenase I that the thrA in the threonine operon encodes has been desensitized.

A further example is the *Escherichia coli* B-5318 strain (see European Patent No. 0593792). The B-5318 strain was deposited under Accession No. VKPM B-5318 at the Russian National Collection of Industrial Microorganisms (VKPM), GNII Genetika (Russia, 117545 Moscow, 1 Dorozhny Proezd, 1) on May 3, 1990. This VKPM B-5318 strain is an isoleucine non-auxotrophic strain, and retains recombinant plasmid DNA constructed in such a way that the gene involved in threonine biosynthesis, i.e., the threonine operon wherein the attenuator region and the native transcriptional regulatory region has been deleted, is located downstream of the lambda phage temperature-sensitive CI repressor, PR promoter, and the N-terminus of Cro protein of lambda phage, and expression of the gene involved in the threonine biosynthesis is controlled by the lambda phage repressor and promoter.

Examples of preferred L-histidine-producing strains include the *Escherichia coli* FERM P-5038 and 5048 strains harboring vectors in which genetic information involved in L-histidine biosynthesis have been incorporated (JP56-005099A), a bacterial strain into which the amino acid export gene Rht has been introduced (EP1016710), and the *Escherichia coli* 80 strain which has resistance to sulfaguanidine, D, L-1,2,4-triazole-3-alanine, and streptomycin (VKPM B-7270, Russian Patent Publication No. 2119536), etc.

Microorganisms in which expression of the gene encoding the L-histidine biosynthesis pathway enzyme may be used to produce L-histidine. Examples of L-histidine biosynthesis enzymes are ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide Isomerase (hisA), amidotransferase (hisH), histidinol phosphate aminotransferase gene (hisC), histidinol phosphatase gene (hisB), and histidinol dehydrogenase gene (hisD), etc.

The preferred L-cysteine-producing bacteria of the present invention are bacteria in which the activity of the cystathionine β-lyase has been reduced (JP2003-169668), and bacteria of the genus *Escherichia* that retain serine acetyltransferase with reduced feedback inhibition by L-cysteine (JP11-155571).

The preferred L-proline-producing bacteria of the present invention include *Escherichia coli* 702 (VKPMB-8011) which is resistant to 3,4-dehydroxyproline and azetidine-2-carboxylate, and 702 ilvA (VKPMB-8012 strain), which is deficient in ilvA, and is derived from 702 (JP 2002-300874A).

Examples of L-phenylalanine-producing bacteria include AJ12739 (tyrA::Tn10, tyrR) (VKPM B-8197) which is deficient in tyrA and tyrR, and strains with amplified genes encoding phenylalanine export proteins, such as yddG and yedA.

Examples of L-arginine-producing bacteria include *Escherichia coli* mutant strains which are resistant to α-methylmethionine, p-fluorophenylalanine, D-arginine, arginine hydroxamic acid, S-(2-aminoethyl)-cysteine, α-methyleserine, β-2-thienylalanine, or sulfaguanidine (JP56-106598), etc. The *Escherichia coli* 237 strain is an L-arginine-producing bacterium that has a mutant which is resistant to feedback inhibition by L-arginine and that retains highly active N-acetyl glutamate synthase, and it is also a preferable L-arginine-producing strain. (EP1170361B). This strain, numbered VKPM B-7925, was deposited with the Russian National Collection of Industrial Microorganisms (VKPM), GNII Genetika on Apr. 10, 2000, and converted to an international deposit under the Budapest Treaty on May 18, 2001. The *Escherichia coli* 382 strain, which is a derivative of the 237 strain and is an L-arginine-producing bacterium with improved acetic acid assimilating ability, may also be used (U.S. Pat. No. 6,841,365). The *Escherichia coli* 382 strain, numbered VKPM B-7926, was deposited with the Russian National Collection of Industrial Microorganisms (VKPM) on Apr. 10, 2000.

Also, as the microorganisms having L-arginine-producing ability, microorganisms with improved expression of genes encoding enzymes involved in L-arginine biosynthesis may be used. Examples of L-arginine biosynthesis enzymes include N-acetyl glutamate synthase (argA), N-acetyl-glutamyl-phosphate reductase (argC), ornithine acetyltransferase (argJ), N-acetyl glutamate kinase (argB), acetyl ornithine transaminase (argD), acetyl ornithine deacetylase (argE), ornithine carbamoyl transferase (argF), argininosuccinate synthase (argG), argininosuccinate lyase (argH), carbamoyl phosphate synthase (carAB), and combinations thereof. After each enzyme name, the name of the gene encoding it is given in parentheses. It is desirable to employ a mutation of the N-acetyl glutamate synthase gene (argA) in which L-arginine feedback inhibition has been removed by substitution of the amino acid sequence corresponding to positions 15 to 19 in the wild-type (EP EP1170361).

The L-leucine-producing bacteria which may be used include a bacterium of the genus *Escherichia coli* in which the branched-chain amino-acid transaminase encoded by the ilvE gene has been inactivated and the activity of the aromatic amino acid transaminase encoded by the tyrB gene has been enhanced (EP1375655A), the *Escherichia coli* H-9068 strain (ATCC21530) which is resistant to 4-azaleucine or 5,5,5-trifluoroleucine, the *Escherichia coli* H-9070 strain (FERM BP-4704), the *Escherichia coli* H-9072 strain (FERM BP-4706) (U.S. Pat. No. 5,744,331), the *Escherichia coli* strain in which the isopropylmalate synthase feedback inhibition by L-leucine has been desensitized (European Patent No. 1067191), the *Escherichia coli* AJ11478 strain which is resistant to β-2 thienylalanine and β-hydroxyleucine (U.S. Pat. No. 5,763,231), and so on.

L-isoleucine-producing bacteria include a 6-dimethyl aminopurine-resistant *Escherichia coli* mutant strain (JP 5-304969A), L-isoleucine hydroxamate-resistant *Escherichia coli* mutant strain (JP5-130882A), thiaisoleucine-resistant *Escherichia coli* mutant strain (JP5-130882A), DL-ethionine-resistant *Escherichia coli* mutant strain (JP5-130882A), and arginine hydroxamate-resistant mutant strain (JP5-130882A), all of which have L-isoleucine-producing ability. Examples of recombinant bacteria of the genus *Escherichia* are bacterial strains in which the expression of the genes encoding the L-isoleucine biosynthesis enzymes threonine deaminase or acetohydroxy acid synthase have been increased (JP2-458A, JP2-42988A, JP 8-47397A), etc.

Examples of parent strains for deriving L-valine-producing bacteria of the present invention include, but are not limited to, strains which have been modified to overexpress the ilvGMEDA operon (U.S. Pat. No. 5,998,178). It is desirable to remove the region in the ilvGMEDA operon which is required for attenuation so that expression of the operon is not attenuated by L-valine. Furthermore, the ilvA gene in the operon is desirably disrupted to decrease threonine deaminase activity.

Examples of parent strains for deriving L-valine-producing bacteria of the present invention include mutants having a mutation in the amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd, 1) on Jun. 24, 1988 under accession number VKPM B-4411.

Furthermore, mutants requiring lipoic acid for growth and/or lacking H+-ATPase can also be used as parent strains (WO96/06926).

Aside from a gene which encodes a native biosynthesis enzyme, a gene which is involved in sugar uptake, sugar metabolism (glycolytic system), and energy metabolism may be enhanced in the L-amino acid-producing bacteria of the present invention.

Examples of the genes involved in sugar metabolism are genes which encode glycolytic enzymes or proteins which uptake sugar, such as genes encoding the glucose-6-phosphate isomerase gene (pgi; WO01/02542), the phosphoenolpyruvate synthase gene (pps), the phosphoglucomutase gene (pgm; WO03/04598), the fructose-bisphosphate aldolase gene (fba; WO03/04664), the pyruvate kinase gene (pykF; WO03/008609), the transaldolase gene (talB; WO03/008611), the fumarase gene (fum; WO01/02545), the phosphoenolpyruvate synthase gene (pps; EP877090), the non-PTS sucrose uptake systems gene (csc; EP149911), and the sucrose-assimilating genes (scrAB operon; WO90/04636).

Examples of the genes involved in energy metabolism include the transhydrogenase gene (pntAB; U.S. Pat. No. 5,830,716) and the cytochromoe bo type oxidase gene (cyoABCD; EP1070376).

<1-2> Method for Increasing the Activity of β-Glucoside PTS

The microorganism of the present invention can be obtained by modifying a microorganism which has the ability to produce an L-amino acid and which belongs to the Enterobacteriaceae family, as described above, so as to increase the enzymatic activity of the β-glucoside PTS. However, the ability to produce an L-amino acid may be imparted after modification to increase the enzymatic activity of the β-glucoside PTS.

An increase in the enzymatic activity of the β-glucoside PTS can be achieved by modifying the expression of the bglF gene which encodes the β-glucoside PTS (described later). The expression of the endogenous bglF gene may be increased through modification of the expression regulatory region, including promoter modification, or the expression of the exogenous bglF gene may be increased by introduction of a plasmid containing the bglF gene, increasing the number of copies by amplifying the bglF gene on the chromosome, etc. Furthermore, a combination of these techniques may be employed.

The β-glucoside PTS in the present invention refers to a permease activity which results in uptake of sugar into the cytoplasm at the same time that the phosphate group in phosphoenolpyruvate (hereinafter, referred to as PEP) is transferred to the β-glucoside. Here, the β-glucoside has 1-D-glucose as the sugar component, for instance, salicin which has been glucoside-linked with salicyl alcohol, or arbutin which has been glucoside-linked to hydroquinone, and generally means a sugar derivative in which various compounds, such as alcohol, phenol, anthocyanin, etc., have been linked to the reduction group of the β-D-glucose. The β-glucoside PTS may also function to transfer the phosphate group, not only to the β-glucoside, but also to the glucose at the same time (*E. coli* & *Salmonella* 2nd Edition American society for Microbiology).

An increase in the enzymatic activity of the β-glucoside PTS can be confirmed by in vitro measurement of the phosphorylating activity, using the method of Chen et al. (Biochemistry 1998 37:8714-8723) (EC 2.7.1.69). Enhancement of the expression of bglF can also be confirmed by comparing the amounts of mRNA of bglF with that in a wild-type or non-modified strain of bacteria. Northern hybridization and RT-PCR can also be used to confirm expression. (Molecular Cloning (Cold Spring Harbor Laboratory Press, Cold Spring Harbor (USA), 2001)). The degree of increase in enzymatic activity is not limited as long as the activity is increased as compared to that in the wild-type or non-modified strain, but it is desirable, for example, for it to be 1.5 or more times, preferably 2 or more times, or more preferably 3 or more times that of the wild or non-modified strain. An increase in the enzymatic activity can be confirmed if the target protein amount is increased relative to that of the non-modified or wild-type strain. This can be detected, for instance, by Western blot using an antibody (Molecular Cloning (Cold Spring Harbor Laboratory Press, Cold spring Harbor (USA), 2001)). The bglF gene of the present invention is derived from or native to the bacteria of the genus *Escherichia* and their homologs. For example, the bglF gene of *Escherichia coli* encodes a protein with the amino acid sequence of SEQ ID No. 6. The gene is registered with Genbank NP_418178 and W3110's sequence is registered with Genbank PTV3B_ECOLI [P08722], both are identical to SEQ ID NO.5. The bglF gene of *Escherichia Coli* is shown in SEQ ID No.5, and the amino acid sequence is shown in SEQ ID No. 6.

The homologs of the bglF gene include those which are derived from or native to other microorganisms, and which have high similarity in structure to the bglF gene of *Escherichia coli*, and which improve the ability to produce an L-amino acid and exhibit β-glucoside PTS activity when introduced into a host. Examples of bglF homologs are the bglF gene from *Erwinia carotovora* (Genbank Accession No. YP_050260), the bglF gene from *Streptococcus agalactiae* (NP-735260), and the bglF gene from *Photorhabdus luminescens* subsp. (NP_927931). Furthermore, based on the homology with the genes given in the above examples, the bglF gene may be cloned from the coryneform group of bacteria, such as *Corynebacterium glutamicum, Brevibacterium lactofermentum*, etc.; the bacteria of the genus *Pseudomonas*, such as *Pseudomonas aeruginosa*, etc.; the bacteria of the genus *Mycobacterium*, such as *Mycobacterium tuberculosis*, etc.; and so forth. For example, the bglF gene may be cloned using synthetic oligonucleotides SEQ ID Nos. 1 and 2.

The genes encoding the β-glucoside PTS used in the present invention are not limited to the wild-type genes, and as long as the function of the encoded β-glucoside PTS protein, i.e., the β-glucoside PTS activity, is not impaired. They can also be a mutant or an artificially modified product encoding a protein which includes a sequence containing several amino acid substitutions, deletions, insertions, additions, or the like at one or multiple positions in the amino acid sequence of SEQ ID No. 6. Here, the term "several" varies with the type and position of the amino acid residues in the stereostructure of the protein. Specifically, it means 1 to 20, preferably 1 to 10, and more preferably 1 to 5. The above substitutions, deletions, insertions, or additions of one or several amino acids are conservative mutations that preserve the β-glucoside PTS activity. A conservative mutation is when substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Preferred conservative substitutions include substitution of Ala by Ser or Thr; the substitution of Arg by Gln, His, or Lys; the substitution of Asn by Glu, Gln, Lys, His, or Asp; the substitution of Asp by Asn, Glu, or Gln; the substitution of Cys by Ser or Ala; the substitution of Gln by Asn, Glu, Lys, His, Asp, or Arg; the substitution of Gly, Asn, Gln, Lys, or Asp; the substitution of Gly by Pro; the substitution of His by Asn, Lys, Gln, Arg, or Tyr; the substitution of Ile by Leu, Met, Val, or Phe; the substitution of Leu by Ile, Met, Val, or Phe; the substitution of Lys by Asn, Glu, Gln, His, or Arg; the substitution of Met by Ile, Leu, Val, or Phe; the substitution of Phe by Trp, Tyr, Met, Ile, or Leu; the substitution of Ser by Thr or Ala; the substitution of Thr by Ser or Ala; the substitution of Trp by Phe or Tyr; the substitution of Tyr by His, Phe, or Trp; and the substitution of Val by Met, Ile, or Leu. Substitutions, deletions, insertions, additions, or inversions and the like of the amino acids described above include ones that have naturally occurred (mutant or variant) due to the differences between species, or individual differences of microorganisms that retain bglF genes. Such genes can be obtained by modifying, using, for instance, the site-specific mutation method, the nucleotide sequence shown in SEQ ID No. 5, so that the site-specific amino acid residue in the protein encoded includes substitutions, deletions, insertions, or additions.

Moreover, the bglF gene homologs can have 80% or above, preferably 90% or above, more preferably 95% or above, even more preferably 97% or above, homology with the amino acid sequence of SEQ No. 6. Since the degenerate code properties of a gene vary with the host into which the gene is introduced, a gene substituted with codons that are more readily utilized by the host is desirable. Likewise, as long as the bglF gene encodes a protein with the function of the β-glucoside PTS, the N terminal or C terminal of the gene may be extended or removed. For example, the number of amino acids which can be extended or removed may be 50 or less, preferably 20 or less, more preferably 10 or less, and even more preferably 5 or less. More specifically, a gene which encodes a protein with from 50 to 5 amino acids extended or removed from either end of SEQ ID No.6 may be used.

Also, a variant of the gene can be obtained by the following conventional mutation treatments. For example, a gene having a nucleotide sequence of SEQ ID No. 5 may be mutated in vitro using hydroxylamine, etc. Another method employs treating the *Escherichia* bacteria with a typical mutation treatment, such as ultraviolet light or a mutation agent, such as N-methyl-N'-nitro-N-nitrosoguanidine (NTG) or Ethyl Methyl Sulfonate (EMS). Whether or not these genes encode a protein that has β-glucoside PTS activity can be confirmed, for example, by expressing these genes in the appropriate cells, and investigating if the ability to uptake β-glucoside has been increased or investigating the phosphorylating activity in vitro employing the method of Chen et al. (Biochemistry 1998 37:8714-8723).

The bglF gene can also be a DNA that hybridizes under stringent conditions with nucleotide sequences complementary to the nucleotide sequences of SEQ ID No.5, or with a probe prepared from these sequences. Here, the term "stringent conditions" refers to conditions under which so-called specific hybrids are formed and nonspecific hybrids are not formed. Although it is difficult to clearly express such conditions in numbers, these can be exemplified as conditions under which highly homologous fragments of DNA, for example, DNA having homology no less than 80%, 90%, or 95%, hybridize with each other and DNAs having homology lower than the above do not hybridize with each other. Alternatively, stringent conditions are exemplified by conditions typical of Southern hybridization washing conditions, which are to wash once or preferably two to three times at a temperature and salt concentration corresponding to 60° C., 1×SSC, 0.1% SDS, preferably 0.1×SSC, 0.1% SDS, and more preferably, 68° C., 0.1×SSC, 0.1% SDS.

DNA containing the nucleotide sequence of SEQ ID No. 5, or a part thereof may also be used as the probe. Such a probe can be prepared using PCR wherein a DNA fragment containing a nucleotide sequence of SEQ ID No. 5 is used as the template, and an oligonucleotide prepared based on the nucleotide sequence of SEQ ID No. 5 as the primer. For example, when using an approx. 300 bp long DNA fragment as the probe, the hybridization washing conditions are 50° C., 2×SSC, and 0.1% SDS.

To enhance the expression of the bglF gene, genetic recombination techniques, for example, can be employed to increase the number of copies of the above-mentioned bglF gene in the cell. For example, a DNA fragment containing the bglF gene is ligated with a vector, preferably a multicopy type vector, which functions in the host microorganism to prepare the recombinant DNA, which is then introduced into the microorganism to transform it.

When the bglF gene of *Escherichia coli* is used, the bglF gene can be obtained by PCR (PCR: polymerase chain reaction; see White, T. J. et al., Trends Genet. 5, 185 (1989)) in which the chromosomal DNA of *Escherichia coli* is the template, and primers are prepared based on the nucleotide sequence of SEQ ID No. 5, for example, the primers shown in SEQ ID Nos. 1 and 2. The bglF genes of other microorganisms belonging to the family Enterobacteriaceae can also be obtained from the known bglF genes in those microorganisms, the bglF genes in microorganisms of other species, chromosomal DNA, or a chromosomal DNA library of microorganisms by PCR wherein the primers are prepared based on the sequence information of the BglF protein, or by hybridization wherein a probe is prepared based on the above-mentioned sequence information. Incidentally, chromosomal DNA can be prepared from DNA donor microorganisms. For example, the method of Saito and Miura, etc. (H. Saito and K. Miura, Biochem. Biophys. Acta, 72, 619 (1963), Seibutsu Kogaku Jikkensho edited by The Society of Biotechnology, Japan, pp. 97-98, Baifukan, 1992) may be used.

Next, the recombinant DNA is prepared by ligating the bglF gene(s) amplified by PCR using a vector DNA capable of functioning in the chosen host microorganism, for example, one which is autonomously replicable in the cells of the host microorganism. Examples of autonomously replicable vectors in cells of *Escherichia coli* include pUC19, pUC18, pHSG299, pHSG399, pHSG398, pACYC184, (pHSG and pACYC are available from Takara Bio Inc.), RSF1010, pBR322, pMW219 (pMW is available from Nippon Gene Co., Ltd.), pSTV29 (available from Takara Bio Inc.), etc.

Recombinant DNA prepared as described above may be introduced into a microorganism in accordance with any of the transformation methods which have been reported to date. For example, the permeability of the DNA can be increased by treating the recipient bacteria with calcium chloride, as reported with regards to *Escherichia coli* K-12 (Mandel, M. and Higa, A., J. Mol. Biol., 53, 159 (1970)). Another method is to introduce the DNA after preparing competent cells from the cells at the growth phase, as reported with regards to *Bacillus subtilis* (Duncan, C. H., Wilson, G. A. and Young, F. E., Gene, 1, 153 (1977)). Also, in relation to *Bacillus subtilis*, actinomycete and yeast, the host microorganism can be changed into the protoplast or spheroplast state that can easily uptake the recombinant DNA, which is then introduced into the DNA recipient bacteria (Chang, S. and Choen, S, N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75 1929 (1978)).

The copy number of the bglF gene can be increased by introducing multiple copies of the bglF gene as described above into the chromosomal DNA of the microorganism. Multiple copies of the bglF gene can be introduced into the chromosomal DNA of the microorganism by homologous recombination, using a a target sequence which is present in multiple copies on the chromosomal DNA. Examples of sequences which are present in multiple copies include repetitive DNA and inverted repeats present on the ends of transposable elements. Also, these genes may be ligated in tandem with the bglF gene present on the chromosome or incorporated by duplication of unnecessary genes on the chromosome. These genes can be introduced using a temperature-sensitive vector or integration vector.

As disclosed JP2-109985A, the bglF gene can be incorporated into a transposon, and the transposon transferred to incorporate multiple copies into the chromosomal DNA. The presence of the gene on the chromosome can be confirmed by Southern hybridization using a part of the bglF gene as a probe.

Aside from increasing the copy number described above, expression of the bglF gene can also be enhanced by employing the methods described in WO00/18935, such as substituting the expression regulatory sequence of the bglF gene promoter, etc., on the chromosomal DNA or plasmid with a stronger one, approximating the −35, −10 regions to the consensus sequence, amplifying a regulator which can enhance the expression of the bglF gene, and deleting or weakening a regulator which would decrease the expression of the bglF gene. For example, the lac promoter, trp promoter, trc promoter, tac promoter, araBA promoter, lambda phage PR promoter, PL promoter, tet promoter, T7 promoter, $\phi$10 promoter, etc., are all known as strong promoters. It is also possible to introduce a base substitution, etc., into the bglF gene's promoter region and SD region to achieve greater promoter strength.

Examples of methods for evaluating the strength of promoters and examples of strong promoters are described in articles by Goldstein et al. (Prokaryotic promoters in biotechnology. Biotechnol. Annu. Rev., 1995, 1, 105-128), etc. Furthermore, the substitution of several nucleotides into the spacer region between the ribosome binding site (RBS) and the start codon, particularly into the sequence immediately upstream of the start codon, is known to have a strong effect on mRNA translation efficiency. These can be modified. The expression regulatory regions of the bglF gene's promoter, etc., can be determined by promoter search vectors and gene analysis software such as GENETYX, etc. Expression of the bglF gene can be strengthened by substitutions or modifications of these promoters. Substitution of expression regulatory sequences can be conducted, for example, by employing temperature-sensitive plasmids or the Red-driven integration method (WO2005/010175).

In order to increase the activity of a protein encoded by bglF gene, a mutation which increases the activity of a β-glucoside PTS may also be introduced into the bglF gene. Examples of mutations which increase the activity of the protein encoded by the bglF gene include a mutation of the promoter sequence, which increases the transcription of the bglF gene, and a mutation within the coding region of the gene, which increases the specific activity of the BglF protein.

<2> Method for Producing L-Amino Acid

The method for producing L-amino acids of the present invention includes culturing the microorganism of the present invention in a medium, allowing the L-amino acid to accumulate in the medium or in the microorganism, and collecting the L-amino acid from the medium or microorganism.

Mediums conventionally used in the fermentation of microorganism to produce L-amino acids may be used in the present invention. That is, an ordinary medium containing a carbon source, nitrogen source, non-organic ions, and other organic components as needed may be used. Carbon sources include a sugar, such as glucose, sucrose, lactose, galactose, fructose, a starch hydrolysase, etc.; an alcohol, such as glycerol, solbitol, etc.; an organic acid, such as fumaric acid, citric acid, succinic acid, etc. Of these, it is preferable to use glucose as the carbon source. Nitrogen sources include an inorganic ammonium salt, such as ammonium sulfate, ammonium chloride, ammonium phosphate, etc., an organic nitrogen, such as a soybean hydrolysis product, etc., ammonia gas, ammonia water, etc. It is desirable for the organic micronutrient sources to contain an appropriate amount of auxotrophic substances, such as vitamin B1, L-homoserine, etc., or yeast extract, etc. In addition to these, according to necessity, small amounts of potassium phosphate, magnesium sulfate, iron ions, manganese ions, etc., can be added. The medium may be either a natural or synthetic medium as long as it contains a carbon source, nitrogen source, inorganic ions, and, as needed, other organic micronutrients.

It is recommended that the culture be performed under aerobic conditions for 1-7 days at a culture temperature of 24° C.-37° C., with a pH during the culture of 5-9. To adjust the pH, an inorganic or organic acidic or alkali substance, and ammonia gas, and the like, may be used. L-amino acids can be collected from the fermentation solution using one or a combination of a conventional methods, such as ion-exchange resin, precipitation, and other known methods. If the L-amino acid accumulates inside the cells of the microorganism, the cells can be crushed by ultrasound, etc., then removed by centrifugal separation to obtain the supernatant, from which the L-amino acid can be collected using an ion-exchange resin method, etc.

It is also possible to use a liquid medium appropriate for production of L-glutamic acid by precipitation, and to perform the culture while the L-glutamic acid is produced and collects in the medium. Conditions for production of L-glutamic acid include, for example, a pH of 5.0-4.0, preferably a pH of 4.5-4.0, more preferably a pH of 4.3-4.0, and even more preferably a pH of 4.0.

Any known recovery method may be used for collecting the L-glutamic acid from the culture solution after completion of the culture. For example, L-glutamic acid can be collected by concentration crystallization after removing the cells from the culture solution, or via ion-exchange chromatography, etc. When culturing under L-glutamic acid producing conditions, the L-glutamic acid which precipitates in the culture solution can also be collected via centrifugal separation, filtering, etc. In this case, the L-glutamic acid dissolved in the culture may be crystallized and then isolated.

Furthermore, an animal feed additive using the produced fermentation broth can be prepared by using a separation method. L-amino acid separation methods such as centrifuging, filtering, decanting, flocculating, or a combination of these can be used to remove or reduce biomass.

The obtained broth can be concentrated using known methods such as a rotary evaporator, thin layer evaporator, reverse osmosis, or nanofiltration (FR8613346B,U.S. Pat. No. 4,997, 754, EP410005B, JP1073646B).

The concentrated broth is then processed using the methods of freeze-drying, spray-drying, spray granulation, or any other process to give a preferably free flowing, finely divided powder. This can then be used as an animal feed additive. This free-flowing finely divided powder can be converted into a coarse-grain, very free flowing, stable and largely dust-free product by using suitable compacting or granulating processes. Altogether, more than 90% of the water is removed in this way so that the water concentration of the animal feed additive is less than 10%, preferably less than 5% by weight.

The protein content of the feed additive can be less than 10%, preferably less than 5% by weight, and the concentration of L-threonine can be more than 50%, preferably more than 85%, more preferably more than 95% (U.S. Pat. No. 5,431,933, JP1214636B, U.S. Pat. Nos. 4,956,471, 4,777, 051, 4,946,654, 5,840,358, 6,238,714, US2005/0025878).

The separation steps described above do not necessarily have to be performed, but may be combined in a technically expedient manner.

EXAMPLES

The present invention will be explained more specifically below with reference to the following non-limiting examples.

Reference Example 1

Construction of an L-Lysine-Producing Bacterium

<1-1> Construction of a Strain in which the cadA and ldcC Genes that Encode Lysine Decarboxylase are Disrupted First, a strain which does not produce lysine decarboxylase was constructed. The Red-driven integration method described in WO WO2005/010175 and a λ phage excision system (J. Bacteriol. 2002 September; 184 (18): 5200-3. Interactions between integrase and excisionase in the phage lambda excisive nucleoprotein complex. Cho E H, Gumport R I, Gardner J F) were used to construct a strain in which lysine decarboxylase genes were disrupted. Lysine decarboxylase is encoded by the cadA gene (Genbank Accession No. NP_418555. SEQ ID No. 42) and the ldcC gene (Genbank Accession No. NP_414728. SEQ ID No. 44) (WO96/17930). The WC196 strain was used as the parent strain. WC196 strain was named *Escherichia coli* AJ13069, and deposited on Dec. 6, 1994 with the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14690 and converted to an international deposit under the Budapest Treaty on Sep. 29, 1995, and given Accession No. FERM BP-5252.

The cadA and ldcC genes encoding lysine decarboxylase were deleted using a method called "Red-driven integration," which was initially developed by Datsenko and Wanner (Proc. Natl. Acad. Sci. USA, 2000, vol. 97, No. 12, pp. 6640-6645), and a λ phage excision system (J. Bacteriol. 2002 September; 184 (18): 5200-3). According to the "Red-driven integration" method, it is possible to construct a gene-disrupted strain in a single step by using a PCR product obtained with a synthetic oligonucleotide primer derived from the 5' terminal end of the target gene and the 3' terminal end of the antibiotic-resistant gene. Furthermore, via λ phage excision, the antibiotic-resistant gene which was integrated into the chromosome can be removed from the strain.

(1) Disruption of the cadA Gene

The pMW118-attL-Cm-attR plasmid described below was used as the PCR template. pMW118-attL-Cm-attR was obtained by inserting the attL and attR-attachment site of α-phage and the cat gene, which is an antibiotic-resistant gene, into pMW118 (Takara Bio Inc.), in the following order: attL-cat-attR (see WO2005/010175). The attL sequence is shown in SEQ ID No. 11, and the attR sequence is shown in SEQ ID No. 12.

PCR was conducted using the synthetic oligonucleotides shown in SEQ ID Nos. 46 and 47 as primers, wherein a sequence corresponding to both ends of attL and attR was at the primer's 3' end and a sequence corresponding to part of the cadA gene, the target gene, was at the primer's 5' end.

The amplified PCR product was purified with an agarose gel, then introduced by electroporation into an *Escherichia coli* WC196 strain containing plasmid pKD46, which has a temperature-sensitive replication origin. Plasmid pKD46 (Proc. Natl. Acad. Sci. USA, 2000, vol. 97, No. 12, pp. 6640-6645) includes the λ phage DNA fragment (2154 bases), and the genes (γ, β, and exo) that encode Red recombinase in the λ Red homologous recombination system under the control of the arabinose-induced ParaB promoter (GenBank/EMBL Accession No. J02459, 31088th-33241st).

Competent cells for electroporation were prepared as follows. The *Escherichia coli* WC196 strain which was cultured overnight at 30° C. in an LB medium containing 100 mg/L ampicillin was diluted 100 times in a 5 mL SOB medium containing ampicillin (20 mg/L) and L-arabinose (1 mM) (Molecular Cloning: Lab Manual 2nd edition, Sambrook, J., et al., Cold Spring Harbor Laboratory Press (1989)). The dilution product was cultured at 30° C. until OD 600 grew to approx. 0.6, and then this was concentrated 100 fold and washed three times with 10% glycerol in preparation for electroporation. Electroporation was performed using 70 µl competent cells and approx. 100 ng PCR product. 1 mL SOC medium (Molecular Cloning: Lab Manual $2^{nd}$ edition, Sambrook, J., et al., Cold Spring Harbor Laboratory Press (1989)) was added and cultured at 37° C. for 2.5 hours, then cultured on a plate medium of L-agar containing Cm (chloramphenicol) (25 mg/L) at 37° C. and the Cm-resistant recombinants were selected. Next, to remove the pKD46 plasmid, cells were subcultured twice on an L-agar medium containing Cm at 42° C., the ampicillin resistance of the colony was tested, and an ampicillin-sensitive strain without pKD46 was obtained.

Deletion of the cadA gene in the mutant identified by the chloramphenicol-resistant gene was confirmed using PCR. The cadA deficient strain was designated WC196ΔcadA::att-cat.

Next, to remove the att-cat gene which is introduced into the cadA gene, a helper plasmid, pMW-intxis-ts, described below, was used. pMW-intxis-contains a gene (SEQ ID No. 13) that encodes λ phage integrase (Int) and a gene (SEQ ID No. 15) that encodes excisionase (Xis) and has temperature-sensitive replication ability. By introducing pMW-intxis-ts, attL (SEQ ID No. 11) and attR (SEQ ID No. 12) on the chromosome are recognized, causing recombination, and the genes between attL and attR are excised, leaving only the attL or attR sequence on the chromosome.

Competent cells of the WC196ΔcadA::att-cat strain obtained as described above were prepared using a typical method, and were transformed with helper plasmid pMW-intxis-ts, cultured on a plate medium of L-agar containing 50 mg/L ampicillin at 30° C., thus selecting the ampicillin-resistant strain. Next, to remove the pMW-intxis-ts plasmid, the transformants were subcultured on an L-agar medium at 42° C., the ampicillin resistance and the chloramphenicol resistance of the colony obtained were tested, and a chloramphenicol-and ampicillin-sensitive strain from which the att-cat and pMW-intxis-ts were removed was obtained. This strain was designated WC196ΔcadA.

(2) Deletion of the ldcC Gene in the WC196ΔcadA Strain

The ldcC gene in the WC196ΔcadA strain was deleted in accordance with the technique described above, using primers having the sequences of SEQ ID Nos. 48 and 49 as the ldcC disrupting primers. This results in WC196ΔcadAΔldcC, in which both cadA and ldcC are disrupted.

(3) Preparation of the PCR Template and Helper Plasmid

The PCR template pMW118-attL-Cm-attR and helper plasmid pMW-intxis-ts were prepared as follows.

(3-1) pMW118-attL-Cm-attR pMW118-attL-Tc-attR was constructed based on pMW118-attL-Cm-attR. The following four DNA fragments were prepared:

1) BglII-EcoRI DNA fragment (120 bp) (SEQ ID No. 11) containing attL obtained by PCR amplification of the sequence corresponding to the chromosome of the *E. coli* W3350 strain (ATCC31278 containing λ prophage), using oligonucleotides P1 and P2 (SEQ ID Nos. 17 & 18) as primers (these primers additionally contained the recognition sites of the BglII and EcoRI endonucleases), 2) PstI-HindIII DNA fragment (182 bp) (SEQ ID No. 12) containing attR obtained by PCR amplification of the sequence corresponding to the chromosome of the *E. coli* W3350 strain (containing λ prophage), using oligonucleotides P3 and P4 (SEQ ID Nos. 19 & 20) as primers (these primers additionally contained the recognition sites of the PstI and HindIII endonucleases), 3) BglII-HindIII large fragment (3916 bp) of pMW118-ter_rrnB: The pMW118-ter_rrnB was obtained by ligating the following three fragments:

i) A large fragment (2359 bp) containing an AatII-EcoRI-pol fragment from pMW118 obtained by digesting the pMW118 with an EcoRI restriction endonuclease, treating it with a Klenow fragment of DNA polymerase I, then digesting the fragment with an AatII restriction endonuclease, ii) An AatII-BglII small fragment (1194 bp) of pUC19 containing the ampicillin-resistant ($Ap^R$) bla gene obtained by PCR-amplifying the sequence corresponding to the pUC19 plasmid, using oligonucleotides P5 and P6 (SEQ ID Nos. 21 & 22) as primers (these primers additionally contained the recognition sites of the AatII and BglII endonucleases), iii) A small BglII-PstIpol fragment (363 bp) containing transcription terminator ter_rrnB obtained by PCR-amplifying the region corresponding to the chromosome of the *E. coli* MG1655 strain, using oligonucleotides P7 and P8 (SEQ ID Nos. 23 & 24) as primers (these primers additionally contained the recognition sites of the BglII and PstI endonucleases), 4) A small EcoRI-PstI fragment (1388 bp) (SEQ ID No. 29) of pML-Tc-ter_thrL containing a tetracycline-resistant gene and transcription terminator ter_thrL. The pML-Tc-ter_thrL was obtained as follows.

A pML-MSC (Mol Biol (Mosk). 2005 September-October; 39(5):823-31; Biotechnologiya (Russian) No. 5: 3-20.) was digested with XbaI and BamHI restriction endonucleases, and a large fragment of this (3342 bp) was ligated with an XbaI-BamHI fragment (68 bp) that contained the terminator ter_thrL. The XbaI-BamHI fragment (68 bp) corresponded to the chromosome of *E. coli* MG1655, and was obtained by PCR amplification, using oligonucleotides P9 and P10 (SEQ ID Nos. 25 & 26) as primers (these primers additionally contained the recognition sites of the XbaI and BamHII endonucleases). The ligated reaction product was designated plasmid pML-ter_thrL.

The pML-ter_thrL was digested with KpnI and XbaI restriction endonucleases, treated with a Klenow fragment of DNA polymerase I, then ligated with a small EcoRI-Van91I fragment (1317 bp) of pBR322 containing the tetracycline-resistant gene (the pBR322 which was digested with EcoRI and Van91I restriction endonucleases was treated with a Klenow fragment of DNA polymerase I). The product of this ligation was designated plasmid pML-Tc-ter_thrL.

Next, the pMW118-attL-Cm-attR was constructed by ligation of a large BamHI-XbaI fragment (4413 bp), a PA2 promoter (initial promoter of T7 phage), a chloramphenicol-resistant (CmR) cat gene, an artificial BglII-XbaI DNA fragment (1162 bp) containing transcription terminator ter_thrL, and attR. The artificial DNA fragment (SEQ ID No. 30) was obtained as follows.

pML-MSC (Mol Biol (Mosk). 2005 September-October; 39(5):823-31; Biotechnologiya (Russian) No. 5: 3-20.) was digested with KpnI and XbaI restriction endonucleases, and ligated with a small KpnI-XbaI fragment (120 bp) containing a PA2 promoter (early promoter of T7 phage). A KpnI-XbaI fragment was obtained by amplifying the region corresponding to T7 phage DNA, using oligonucleotides P11 and P12 (SEQ ID Nos. 27 & 28) as primers (these primers additionally contained the recognition sites of the KpnI and XbaI endonucleases) by PCR. The product of the ligation was designated plasmid pML-PA2-MCS.

The XbaI site was removed from pML-PA2-MCS. The product was designated plasmid pML-PA2-MCS(XbaI-).

A small BglII-HindIII fragment (928 bp) of pML-PA2-MCS(XbaI-) containing a PA2 promoter (initial promoter of T7 phage) and chloramphenicol-resistant (CmR) cat gene was ligated with a small HindIII-HindIII fragment (234 bp) of pMW118-attL-Tc-attR, which contained the transcription terminator ter_thrL, and attR.

The target artificial DNA fragment (1156 bp) was obtained by PCR amplification of the ligation mixture, using oligonucleotides P9 and P4 (SEQ ID Nos. 25 & 20) as primers (these primers contained the recognition sites of the HindIII and XbaI endonucleases).

(3-2) pMW-intxis-ts

First, two DNA fragments were amplified based on λ phage DNA (Fermentas) as the template. The first fragment consisted of a region of nt 37168-38046 of the genome of λ phage DNA (SEQ ID No. 39), and contained a cI repressor, Prm and Pr promoters, and the leader sequence of the cro gene. This fragment was obtained by amplification, using oligonucleotides P1' and P2' (SEQ ID Nos. 31 & 32) as primers. The second fragment consisted of a region of nt 27801-29100 of the genome of K phage DNA (SEQ ID No. 40), which contained the xis-int gene from K phage DNA. This fragment was obtained by PCR, using oligonucleotides P3' and P4' (SEQ ID Nos. 33 & 34) as primers. All of the primers contained the proper endonuclease recognition sites.

The first PCR-amplified fragment, which contained the cI repressor, was digested with a ClaI restriction endonuclease, and then digested with EcoRI restriction endonuclease.

The second PCR fragment was digested with EcoRI and PstI endonucleases. The plasmid pMWPlaclacI-ts was digested with BglII endonuclease, treated with a Klenow fragment of DNA polymerase I, and then digested with a PstI restriction endonuclease. A vector fragment of pMWPlaclacI-ts was eluted from an agarose gel and ligated with the cut PCR-amplified fragment.

The plasmid pMWPlaclacI-ts is a derivative of pMWPlaclacI containing the following parts: 1) an artificial BglII-HindIII DNA fragment containing a PlacUV5 promoter and the lacI gene under control of the RBS of the bacteriophage T7 gene 10; 2) an AatII-BglII fragment containing the ampicillin-resistant (Ap$^R$) gene obtained by PCR amplification of the region corresponding to the pUC19 plasmid, using oligonucleotides P5' and P6' (SEQ ID Nos. 35 & 36) as primers (these primers contained the recognition sites of the AatII and BglII endonucleases); 3) an AatII-HindIII fragment containing an AatII-PvuI fragment of a recombinant plasmid pMW118-ter_rrnB. The plasmid pMW118-ter_rrnB was constructed as follows. A PstI-HindIII fragment containing a terminator ter_rrnB was obtained by PCR amplification of the region corresponding to the chromosome of the E. coli MG1655 strain, using as primers oligonucleotides P7' and P8' (SEQ ID Nos. 37 & 38) which contained the proper endonuclease recognition sites. Prior to ligation, the pMW118 and ter_rrnB fragments (complementary strand of SEQ ID No. 41) were digested with PvuI or PstI, respectively, treated with a Klenow fragment of DNA polymerase I to blunt the ends, and then digested with AatII or HindIII endonuclease. In the construction of the pMWPlaclacI-ts mutant, an AatII-EcoRV fragment of plasmid pMWPlaclacI was substituted with an AatII-EcoRV fragment of plasmid pMAN997 which contained the par, ori, and repAts genes of the pSC101 replicon. (Applied and Environmental Microbiology, June 2005, p. 3228-32)

Example 1

Construction of Plasmid for bglF Overexpression

The total genome sequence of the chromosome of *Escherichia coli* (*Escherichia coli* K-12 strain) has been determined (Science, 277, 1453-1474 (1997)). Based on the nucleotide sequence of the bglF gene, using as a 5' primer the synthetic oligonucleotide of SEQ ID No.1 having a HindIII site, and as a 3' primer the synthetic oligonucleotide of SEQ ID No.2 having an XbaI site, PCR was performed using chromosomal DNA of the *Escherichia Coli* MG1655 strain as the template. The PCR product was treated with restriction endonucleases HindIII and XbaI, and a gene fragment that contained the bglF genes was obtained.

The purified PCR product was ligated with vector pMW219 which had been digested with HindIII and XbaI (Nippon Gene Co., Ltd.) to construct a plasmid pM-bglF for bglF overexpression. This plasmid was under the control of a lac promoter and the bglF gene was placed downstream of the lac promoter. pM-bglF was digested with HindIII and EcoRI, the bglF gene fragments were collected and purified, and ligated to vector pSTV29 which had been digested with HindIII and EcoRI (Takara Shuzo). In this way, the plasmid pS-bglF for bglF overexpression was constructed.

In the same manner as with the above-mentioned bglF gene, a plasmid for expressing the ptsG gene was constructed as the control. The sequence of ptsG is shown in SEQ ID No. 7 and the sequence of the amino acid is given in SEQ ID No. 8; the ptsG sequence can be obtained with reference to Genbank Accession No. NP_415619. Using as a 5' primer the synthetic oligonucleotide of SEQ ID No.3 containing a HindIII site, and as a 3' primer the synthetic oligonucleotide of SEQ ID No.4 containing an XbaI site, PCR was performed using the chromosomal DNA of the *Escherichia Coli* MG1655 strain as the template, and the PCR fragment was treated with restriction endonucleases HindIII and XbaI, and a gene fragment containing ptsG was obtained. The purified PCR product was ligated with vector pMW219, which had been digested with HindIII and XbaI, to construct plasmid pM-ptsG for ptsG overexpression. This plasmid was under the control of a lac promoter, and the ptsG gene was placed downstream of the lac promoter. In the same manner as with the bglF, the ptsG gene fragment was excised from the pM-ptsG, and ligated to vector pSTV29. In this way, the plasmid pS-ptsG for ptsG overexpression was constructed.

Example 2

Construction of the Strain in which the bglF Gene is Overexpressed and Evaluation of L-Lysine Production of the Strain As an *Escherichia coli* L-lysine-producing strain, the WC196ΔldcCΔcadA (pCABD2) strain was used as parent strain. Lys-producing plasmid pCABD2 carrying the dapA, dapB, and lysC genes (WO01/53459) was introduced into the WC196ΔldcCΔcadA strain. The WC196ΔldcCΔcadA (pCABD2) strain was transformed with the bglF-overexpression plasmid pM-bglF and the ptsG-overexpression plasmid pM-ptsG constructed in Example 1, and the control plasmid pMW219, and kanamycin-resistant strains were obtained. After confirming that these plasmids had been introduced, the bglF-overexpression plasmid pM-bglF-introduced strain was designated WC196ΔldcCΔcadA (pCABD2, pM-bglF); the ptsG-overexpression plasmid pM-ptsG-introduced strain was designated WC196ΔldcCΔcadA (pCABD2, pM-ptsG); and the control plasmid pMW219-introduced strain was designated WC196ΔldcCΔcadA (pCABD2, pMW219).

The strains constructed as described above were cultured in an L medium containing 25 mg/L kanamycin at 37° C. to finally become OD600 0.6. Then, an equal volume of a 40% glycerol solution was added to the culture and stirred, then appropriate amounts were pipetted and stored at −80° C. This was called the glycerol stock.

After melting the glycerol stock of these strains, 100 μL of each was evenly spread onto an L plate containing 25 mg/L kanamycin, and this was cultured at 37° C. for 24 hours. Approx. ⅛ of the cells on the plate were inoculated into a 20 mL fermentation medium (shown below) with 25 mg/L kanamycin in a 500 mL Sakaguchi shaking flask, and cultured at 37° C. for 24 hours using a reciprocating shaking culture apparatus. After culturing, the amount of lysine which had accumulated in the medium was measured using a Biotech-analyzer AS210 (Sakura Seiki).

The OD and L-lysine which had accumulated at the 24th hour are shown in Table 1. As evident in Table 1, a large amount of L-lysine accumulated in the WC196ΔldcCΔcadA (pCABD2, pM-bglF) strain, compared to the WC196ΔldcCΔcadA (pCABD2, pMW219) strain which did not contain the bglF genes. An improvement in the amount of L-lysine which accumulated was also confirmed in comparison with the WC196ΔldcCΔcadA (pCABD2, pM-ptsG) strain, which did contain the ptsG gene. Such data shows that overexpression of the bglF gene is more effective in lysine production than overexpression of the ptsG.

TABLE 1

| Bacterial strain | OD600 | Lys-HCl(g/L) |
| --- | --- | --- |
| WC196ΔldcCΔcadA (pCABD2, pMW219) | 12.6 | 10.0 |
| WC196ΔldcCΔcadA (pCABD2, pM-bglF) | 17.1 | 16.1 |
| WC196ΔldcCΔcadA (pCABD2, pM-ptsG) | 15.8 | 14.7 |

Medium for L-Lysine Production:

| | |
| --- | --- |
| Glucose | 40 g/L |
| Ammonium sulfate | 24 g/L |
| Potassium Dihydrogen Phosphate | 1.0 g/L |
| Magnesium sulfate 7-hydrate | 1.0 g/L |
| Ferrous sulfate 4•7-hydrate | 0.01 g/L |
| Manganese sulfate 4•7-hydrate | 0.01 g/L |
| Yeast extract | 2.0 g/L |
| Calcium carbonate | 30 g/L |

Adjusted to pH 7.0 with KOH, and sterilized at 115° C. for 10 min.
Glucose and MgSO₄•7H₂O were sterilized separately.

Example 3

Effect of bglF Overexpression on an L-Glutamic Acid-Producing Strain of *Escherichia* Bacteria As an *Escherichia coli* L-glutamic acid-producing strain, the AJ12949 strain was used as the parent strain. The AJ12949 strain is a bacterial strain in which the α-ketoglutarate dehydrogenase activity has been reduced, and was deposited on Dec. 28, 1993 with the National Institute of Bioscience and Human Technology of the Agency of Industrial Science and Technology (currently, International Patent Organism Depositary, National Institute of Advanced Industrial Science and Technology; Chuo 6, 1-1, Higashi 1-chome, Tsukuba-shi, Ibaraki-ken 305-8566, Japan) under Accession No. FERM P-14039 and converted to an international deposit under the Budapest Treaty on Nov. 11, 1994, and given Accession No. FERM BP-4881.

The AJ12949 strain was transformed with the bglF-overexpression plasmid pS-bglF used in Example 1, and the control plasmid pSTV29, and chloramphenicol-resistant strains were obtained. After confirming that the plasmids had been introduced, the strain into which the bglF-overexpression plasmid pS-bglF was introduced was designated AJ12949 (pS-bglF); and the strain into which the control plasmid pSTV29 was introduced was designated AJ12949 (pSTV29).

The AJ12949 (pS-bglF) strain and the AJ12949 (pSTV29) strain were cultured in an L medium containing 20 mg/L chloramphenicol at 37° C. to finally become OD600 0.6. After this, an equal volume of a 40% glycerol solution was added to the culture and stirred, then appropriate amounts were pipetted to obtain a glycerol stock and stored at −80° C.

After melting the glycerol stock of these strains, 100 μL of each was evenly spread onto an L plate containing 20 mg/L chloramphenicol, and cultured at 37° C. for 24 hours. Approx. ⅛ of the cells on the plate were inoculated into a 20 mL fermentation medium (described below) with 20 mg/L chloramphenicol in a 500 mL Sakaguchi flask, and cultured at 37° C. for 40 hours using a reciprocating shaking culture apparatus. After culturing, the amount of L-glutamic acid which had accumulated in the medium was measured using a Biotech-analyzer AS210 (Sakura Seiki).

The OD and L-glutamic acid which had accumulated at the 40$^{th}$ hour are shown in Table 2. As shown in Table 2, a large amount of L-glutamic acid had accumulated in the AJ12949 (pS-bglF) strain, compared to the AJ12949 (pSTV29) strain which did not contain the bglF genes.

TABLE 2

| Bacterial strain | OD600 | L-Glu (g/L) |
| --- | --- | --- |
| AJ12949 (pSTV29) | 14.7 | 18.6 |
| AJ12949 (pS-bglF) | 16.6 | 20.4 |

Medium for L-Glutamic Acid-Production:

| | |
| --- | --- |
| Glucose | 40 g/L |
| Ammonium sulfate | 20 g/L |
| Potassium Dihydrogen Phosphate | 1.0 g/L |
| Magnesium sulfate 7-hydrate | 1.0 g/L |
| Ferrous sulfate 4•7-hydrate | 0.01 g/L |
| Manganese sulfate 4•7-hydrate | 0.01 g/L |
| Yeast extract | 2.0 g/L |
| Calcium carbonate | 30 g/L |

Adjusted to pH 7.0 with KOH, sterilized at 115° C. for 10 min.

Glucose and MgSO4.7H₂O were sterilized separately.
Also, after the culture temperature was at 60° C. or below, a thiamine hydrochloride solution which had been sterilized with a DISMIC-25cs 0.2 mm filter (ADVANTEC) was added to obtain the final concentration of 0.01 g/L.

Example 4

Effect of bglF Overexpression on an L-Threonine-Producing Strain of Bacteria of the Genus *Escherichia*

As the parent strain of the bglF overexpression for L-threonine-production, the B-5318 strain was used. The B-5318 strain was deposited on May 3, 1990 with the Russian National Collection of Industrial Microorganisms (VKPM), GNII Genetika (Russia, 117545 Moscow, 1 Dorozhny Proezd, 1) under Accession No. VKPM B-5318. The construction of the bglF overexpression strain from B-5318 was performed using the plasmid as described in Example 1.

The B-5318 strain was transformed with the bglF-amplifying plasmid pS-bglF used in Example 1 and the control plasmid pSTV29, and chloramphenicol-resistant strains were obtained. After confirming that the prescribed plasmids had been introduced, the strain into which bglF-overexpression plasmid pS-bglF was introduced was designated B-5318 (pS-bglF); and the strain into which control plasmid pSTV29 was introduced was designated B-5318 (pSTV29).

The B-5318 (pS-bglF) strain and the B-5318 (pSTV29) strain were cultured in an L medium containing 20 mg/L chloramphenicol at 37° C. to finally become OD600 0.6. After this, an equal volume of a 40% glycerol solution was added to the culture and stirred, then appropriate amounts were pipetted to obtain a glycerol stock and stored at −80° C.

After melting the glycerol stock of these strains, 100 µL of each was evenly spread onto an L plate containing 20 mg/L chloramphenicol, and cultured at 37° C. for 24 hours. Approx. ⅛ of the cells on the plate were inoculated into a 20 mL fermentation medium with 20 mg/L chloramphenicol in a 500 mL Sakaguchi shaking flask, and cultured at 37° C. for 16 hours using a reciprocating shaking culture apparatus. After culturing, the amount of L-threonine which had accumulated in the medium was measured using high-performance liquid chromatography.

The OD and L-threonine which had accumulated at the 16th hour are shown in Table 3. As shown in the table, a large amount of L-threonine had accumulated in the B-5318 (pS-bglF) strain, compared to the B-5318 (pSTV29) strain, which did not contain the bglF gene.

TABLE 3

| Bacterial strain | OD600 | L-threonine (g/L) |
|---|---|---|
| B-5318 (pSTV29) | 8.0 | 3.6 |
| B-5318 (pS-bglF) | 10.3 | 4.4 |

Medium for L-Threonine-Production:

| | |
|---|---|
| Glucose | 60 g/L |
| Ammonium sulfate | 16 g/L |
| Potassium Dihydrogen Phosphate | 0.7 g/L |
| Magnesium sulfate 7-hydrate | 1.0 g/L |
| Ferrous sulfate 7-hydrate | 0.01 g/L |
| Manganese sulfate 7-hydrate | 0.01 g/L |
| Yeast extract | 0.5 g/L |
| Thiamine hydrochloride | 0.2 mg/L |
| L-isoleucine | 0.05 g/L |
| Calcium carbonate | 30 g/L |

Adjusted to pH 7.0 with KOH, sterilized at 115° C. for 10 min.

However, glucose and $MgSO_4 \cdot 7H_2O$ were sterilized separately. Potassium hydroxide was sterilized by dry heat at 180° C. for 3 hours. After the culture temperature came down to 60° C. or lower, a thiamine hydrochloride solution which had been sterilized with a DISMIC-25cs 0.2 mm filter (ADVANTEC) was added to obtain the final concentration of 0.2 mg/L.

Example 5

Effect of bglF Overexpression on an L-Glutamic Acid-Producing Strain of *Pantoea* Bacteria As the parent strain of the bglF amplification L-glutamic acid-producing strain, the *Pantoea ananatis* AJ13601 strain can be used. The *Pantoea ananatis* AJ13601 strain was deposited on Aug. 18, 1999 with the National Institute of Bioscience and Human Technology, Agency of Industrial Science and Technology, Ministry of Economy, Trade and Industry (1-3, Higashi 1-chome, Tsukuba-shi, Ibaraki-ken 305-8566) under Accession No. FERM P-17516 and converted to an international deposit under the Budapest Treaty on Jul. 6, 2000, and given Accession No. FERM BP-7207. The bglF amplified strains can be constructed from L-glutamic acid-producing bacteria using the plasmid described in Example 1.

The bglF overexpressed strains are cultured in an L-glutamic acid-production medium and cultured using a reciprocating shaking culture apparatus. After culturing, the amount of L-glutamic acid which had accumulated in the medium is measured using Biotech-analyzer AS210 (Sakura Seiki) to confirm whether the accumulation of L-glutamic acid has increased. In this way, the bglF overexpressed strain with an improved L-glutamic acid-producing ability can be obtained.

While the invention has been described in detail with reference to preferred embodiments thereof, it will be apparent to one skilled in the art that various changed can be made, and equivalents employed, without departing from the scope of the invention. All documents cited herein are hereby incorporated by reference.

The invention claimed is:

1. A method for producing an L-amino acid comprising:

A) culturing in a medium an *Escherichia coli* bacterium which has an ability to produce an L-amino acid and which has been modified to enhance β-glucoside PTS activity as compared to a corresponding non-modified microorganism, and B) collecting the L-amino acid from the medium or the microorganism;

wherein said activity is enhanced by increasing expression of the bglF gene by a method selected from the group consisting of:

A) increasing the copy number of the gene,

B) modifying an expression regulatory sequence of the gene, and

C) combinations thereof.

2. The method according to claim 1, wherein said bglF gene is selected from the group consisting of:

(a) a DNA comprising the nucleotide sequence of SEQ ID NO. 5, and
(b) a DNA encoding a protein having β-glucoside PTS activity which hybridizes with a DNA comprising a sequence fully complementary to the nucleotide sequence of SEQ ID NO. 5 under stringent conditions comprising washing at 60° C., in a salt concentration of 1×SSC, 0.1% SDS.

3. The method according to claim 1, wherein the bglF gene encodes a protein selected from the group consisting of:

(A) a protein comprising the amino acid sequence of SEQ ID NO.6, and
(B) a protein comprising an amino acid sequence which is at least 95% homologous to the amino acid sequence of SEQ ID NO.6, and has β-glucoside PTS activity.

4. The method according to claim 1, wherein said L-amino acid is selected from the group consisting of L-lysine, L-threonine, L-glutamic acid, and combinations thereof.

* * * * *